US007491798B2

(12) United States Patent
Boyd et al.

(10) Patent No.: US 7,491,798 B2
(45) Date of Patent: Feb. 17, 2009

(54) SCYTOVIRINS AND RELATED CONJUGATES, FUSION PROTEINS, NUCLEIC ACIDS, VECTORS, HOST CELLS, COMPOSITIONS, ANTIBODIES AND METHODS OF USING SCYTOVIRINS

(75) Inventors: Michael R. Boyd, Mobile, AL (US); Heidi R. Bokesch, Frederick, MD (US); Barry R. O'Keefe, Frederick, MD (US); Tawnya C. McKee, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 289 days.

(21) Appl. No.: 10/513,961

(22) PCT Filed: May 15, 2003

(86) PCT No.: PCT/US03/15991

§ 371 (c)(1),
(2), (4) Date: Dec. 20, 2004

(87) PCT Pub. No.: WO03/097814

PCT Pub. Date: Nov. 27, 2003

(65) Prior Publication Data

US 2005/0084496 A1 Apr. 21, 2005

Related U.S. Application Data

(60) Provisional application No. 60/381,322, filed on May 16, 2002.

(51) Int. Cl.
*C07K 14/195* (2006.01)
*C07H 21/00* (2006.01)
*A61K 38/00* (2006.01)
*C12N 5/00* (2006.01)
*C12N 1/00* (2006.01)
*C12N 1/20* (2006.01)
*C12N 1/14* (2006.01)
*C12N 15/00* (2006.01)

(52) U.S. Cl. .................. 530/350; 514/2; 435/325; 435/243; 435/252.1; 435/254.2; 435/320.1; 536/23.1; 536/23.7

(58) Field of Classification Search .................. None
See application file for complete search history.

(56) References Cited

U.S. PATENT DOCUMENTS

| 5,314,995 A | 5/1994 | Fell, Jr. et al. |
| 5,821,081 A | 10/1998 | Boyd et al. |
| 5,843,882 A | 12/1998 | Boyd et al. |
| 5,962,653 A | 10/1999 | Boyd et al. |
| 5,962,668 A | 10/1999 | Boyd et al. |
| 5,998,587 A | 12/1999 | Boyd et al. |
| 6,015,876 A | 1/2000 | Boyd |
| 6,183,961 B1 * | 2/2001 | Bernstein et al. ............ 435/6 |
| 6,193,982 B1 * | 2/2001 | Boyd ...................... 424/208.1 |
| 6,245,737 B1 | 6/2001 | Boyd et al. |
| 6,428,790 B1 | 8/2002 | Boyd |

FOREIGN PATENT DOCUMENTS

WO    WO 93/06216    4/1993

OTHER PUBLICATIONS

Gait et al., "Progress in anti-HIV structure-based drug design," Trends in Biotechnology, vol. 13 No. 10, pp. 430-438 (Oct. 1995).*
Marcus et al., "HIV: epidemiology and strategies for therapy and vaccination," Intervirology, vol. 45 No. 4-6, pp. 260-266 (Jul.-Dec. 2002).*
Molla et al., "Evolving therapeutic paradigms for HIV and HCV,"Current Opinion in Biotechnology, vol. 14 No. 6, pp. 634-640 (Dec. 2003).*
Berkley et al., "Scientific and policy challenges to development of an AIDS vaccine," The Lancet, vol. 370 No. 9581, pp. 94-101 (Jul. 2007).*
McFeeters et al., "The novel fold of scytovirin reveals a new twist for antiviral entry inhibitors," Journal of Molecular Biology, vol. 369 No. 2, pp. 451-461 (Mar. 2007).*
Ziolkowska et al., "Structural studies of algal lectins with anti-HIV activity," Acta biochimica Polonica, vol. 53 No. 4, pp. 617-626 (Nov. 2006).*
Agnew et al., *Sex. Trans. Dis.*, 22(5), 269-273 (1995).
Amon et al., *The Plant Cell*, 10, 781-789 (1998).
Andorfer et al., *J. Insect Phys.*, 46, 365-372 (2000).
Andreu et al., *J. Infect. Dis.*, 171, 1237-1243 (1995).
Aullo et al., *EMBO J.*, 11(2), 575-583 (1992).
Balzarini et al., *Antiviral Res.*, 18, 191-207 (1992).
Berzofsky, *J. Acquired Immune Deficiency Syndromes*, 4, 451-459 (1991).
Bolmstedt et al., *Mol. Pharmacology*, 59(5), 949-954 (2001).
Boyd et al., *Antimicrob. Agents Chemother.*, 41(7), 1521-1530 (1997).
Boyd, *AIDS Etiology, Diagnosis, Treatment, and Prevention*, 2nd Ed., 305-317 (1988).
Boyd et al., *J. Med. Chem.*, 37, 1740-1745 (1994).
Bruce et al., *Can. J. Microbiol.*, 34, 339-343 (1988).
Buckheit et al., *Antiviral Res.*, 21, 247-265 (1993).
Cammack, *Curr. Opin. Infect. Dis.*, 14, 13-16 (2001).
Capon et al., *Annu. Rev. Immunol.*, 9, 649-678 (1991).
Capon et al., *Nature*, 337, 525-531 (1989).
Carone et al., *J. Lab. Clin. Med.*, 100(1), 1-14 (1982).
Carter et al., *J. Org. Chem.*, 49, 236-241 (1984).
Charan et al., *J. Nat. Prod.*, 63, 1170-1174 (2000).
Chaudhary et al., *The Human Retroviruses*, Ch. 18, 379-387 (1991).
Chaudhary et al., *Nature*, 335, 369-372 (1988).
Clanton et al., *J. Acquired Immuned Deficiency Syndromes*, 5, 771-781 (1992).

(Continued)

*Primary Examiner*—Zachariah Lucas
(74) *Attorney, Agent, or Firm*—Leydig, Voit & Mayer, Ltd.

(57) ABSTRACT

An isolated or purified antiviral protein of SEQ ID NO: 1, nucleic acids encoding the antiviral protein, cells comprising the nucleic acids, and methods of inhibiting viral infection comprising contacting the virus with the antiviral protein.

46 Claims, 4 Drawing Sheets

OTHER PUBLICATIONS

Coffin, *Science*, 267, 483-489 (1995).
Cohen, *Science*, 267, 179 (1995).
Cresswell et al., *Algal and Cyanobacterial Biotechnology*, 211-218 (1989).
Davey et al., *J. Infect. Dis.*, 170, 1180-1188 (1994).
Davis, *J. Pharm. Pharmacol.*, 44(Suppl. 1), 186-190 (1992).
De Clercq, *Adv. In Virus Res.*, 42, 1-55 (1993).
De Clercq, *J. Acquired Immune Deficiency Syndromes*, 4(3), 207-218 (1991).
Does et al., *Plant Mol. Biol.*, 39, 335-347 (1999).
Dorsey et al., *Protease Inhibitors in AIDS Therapy, Ch. 4*, 65-84, no date available.
Duncan et al., *Protease Inhibitors in AIDS Therapy, Ch. 2*, 27-48, no date available.
Elmer et al., *JAMA*, 275(11), 870-876 (1996).
Faulkner, *Nat. Prod. Rep.*, 355-394 (1994).
Flint et al., *Virlogy Molecular Biology, Pathogenesis, and Control, Ch. 19*, 662-714 (2000).
Frankmolle et al., *J. Antibiotics*, 45(9), 1451-1457 (1992).
Freed et al., *Bull. Inst. Pasteur.*, 88, 73-110 (1990).
Fung et al., *J. Immunology*, 145(7), 2199-2206 (1990).
Gartner et al., *Techniques in HIV Research, Ch. 3*, 59-63 (1994).
Gulakowski et al., *J. Virol. Methods*, 33, 87-100 (1991).
Gustafson et al., *J. Med. Chem.*, 35, 1978-1986 (1992).
Harata et al., *J. Mol. Biol.*, 297, 673-681 (2000).
Hilier et al., *Clin. Infect. Dis.*, 16(Suppl 4), S273-S281 (1993).
Hols et al., *Appl. and Environ. Microbiol.*, 60(5), 1401-1413 (1994).
Husson et al., *J. Pediatr.*, 121(4), 627-633 (1992).
Kashman et al., *J. Med. Chem.*, 35, 2735-2743 (1992).
Kemptf, *Protease Inhibitors in AIDS Therapy, Ch. 3*, 49-64, no date available.
Kilby et al., *Nature Medicine*, 4(11), 1302-1307 (1998).
Krishnamurthy et al., *PNAS USA*, 86, 770-774 (1989).
Langner et al., *Arch. Virol.*, 130, 157-170 (1993).
Lifson et al., *J. Exp. Med.*, 164, 2101-2106 (1986).
Lin et al., *Animicrob Agents Chemother.*, 33(12), 2149-2151 (1989).
Liou et al., *Biochemistry*, 38, 11415-11424 (1999).
Lipton, *Nature*, 367, 113-114 (1994).
Matsushita et al., *J. Virology*, 62(6), 2107-2114 (1988).
McGroarty, *FEMS Immunol. Med. Microbiol.*, 6, 251-264 (1993).
Merigan, *Amer. J. Med.*, 90(Suppl. 4A), 8S-17S (1991).
Michalowski et al., *Nucleic Acids Res.*, 18(8), 2186 (1990).
Mitsuya et al., *Science*, 249, 1533-1544 (1990).
Moore et al., *J. Virology*, 66(1), 235-243 (1992).
Morgan et al., *AIDS Research and Human Retroviruses*, 10(11), 1507-1515 (1994).
Okino et al., *Tetrahedron Ltrs.*, 34(3), 501-504 (1993).
Orloff et al., *AIDS Research and Human Retroviruses*, 11(3), 335-342 (1995).
Patterson et al., *J. Phycol.*, 27, 530-536 (1991).
Patterson et al., *J. Phycol.*, 29, 125-130 (1993).
Polsky et al., *Contraception*, 39(6), 579-587 (1989).
Ramachandran et al., *JID*, 170, 1009-1013 (1994).
Redondo-Lopez et al., *Reviews Infect. Dis.*, 12(5), 856-872 (1990).
Reich, *Protease Inhibitors in AIDS Therapy, Ch. 5*, 85-99, no date available.
Reid et al., *Clinical Microbiol. Reviews*, 3(4), 335-344 (1990).
Rosenberg et al., *Amer. J. Pub. Health*, 82(11), 1473-1478 (1992).
Rosenberg et al., *Sexually Transmitted Diseases*, 20(1), 41-44 (1993).
Royer et al., *Pharmacol. Res.*, 24(4), 407-412 (1991).
Rumbeli et al., *FEBS Ltrs.*, 221(1), 1-2 (1987).
Sattentau et al., *AIDS*, 2(2), 101-105 (1988).
Schaeffer et al., *Ecotoxicology and Evironmental Safety*, 45, 208-227 (2000).
Schooley et al., *Annals of Internal Medicine*, 112(4), 247-253 (1990).
Shenoy et al., *J. Pharmacol. Exp. Ther.*, 297(2), 704-710 (2001).
Sherman et al., *The Cyanobacteria, Ch. 1*, 1-33 (1987).
Shih et al., *PNAS USA*, 88, 9878-9882 (1991).
Sivonen et al., *Chem. Res. Toxicol.*, 5(4), 464-469 (1992).
Suter et al., *FEBS Ltrs.*, 217(2), 279-282 (1987).
Swanson et al., *J. Biol. Chem.*, 267(23) 16146-16154 (1992).
Taylor, *J. NIH Res.*, 6, 26-27 (1994).
Theiβ et al., *Meth. Find. Exp. Clin. Pharmacol.*, 13(5), 353-359 (1991).
Till et al., *Science*, 242, 1166-1168 (1988).
Traunecker et al., *Nature*, 339, 68-70 (1989).
Tung et al., *Protease Inhibitors in AIDS Therapy, Ch. 6*, 101-118, no date available.
Verhoef et al., *Eur. J. Drug Metab. Phartmacokinet.*, 15(2), 83-93 (1990).
Wallace et al., *Science*, 260, 912-913 (1993).
Weislow et al., *J. Natl. Cancer Inst.*, 81(8), 577-586 (1989).
White et al., *Antiviral Res.*, 16, 257-266 (1991).
Wunsch, *Biopolymers*, 22, 493-505 (1983).
Yeh et al., *PNAS USA*, 89, 1904-1908 (1992).
Zaghouani et al., PNAS USA, vol. 88, 5645-5649 (1991).
Bokesch et al., *Biochemistry*, 42:2578-2584 (2003).
Gustafson et al., *Biochemical and Biophysical Research Communications*, 238(No. 1):223-228 (1997).
Adams et al., "Oligosaccharide and glycoprotein microarrays as tools in HIV glycobiology; glycan-dependent gp120/protein interactions," *Chem. Biol.*, 11, 875-881 (2004).
Bewley et al., "Solution structure of cyanovirin-N, a potent HIV-inactivating protein," *Nat. Struct. Biol.*, 5(7), 571-578 (1998).
Botos et al., "Structures of the complexes of a potent anti-HIV protein cyanovirin-N and high mannose oligosaccharides," *J. Biol. Chem.*, 277(37), 34336-34342 (2002).
McFeeters et al., "The novel fold of scytovirin reveals a new twist for antiviral entry inhibitors," *J. Mol. Biol.*, 369, 451-461 (2007).
Xiong et al., "Potent anti-HIV activity of scytovirin domain 1 peptide," *Peptides*, 27, 1668-1675 (2006).

* cited by examiner

```
GSGPT YCWNE ANDPG GPNRC SHNKQ CDGAR TCSSS GFCQG TSRXP DPG
 |||  |||:|  |  |||  |||||  ||:||  |||||  |||||  |||||  |
PKGPT YCWDE AKNPG GPNRC SHSKQ CDGAR TCSSS GFCQG TAGHA AA   (SEQ ID NO: 1)
```

FIGURE 2

```
scytovirin   GSGPTYCWNEAKNPGGPNRCS---NNKQCDGARTCSSSGPCQQTSRKPDPGP-----  49
              :|  ||||  ||  |||||||: :|||||||||||||||||||  |||  |
CL-B         QKSASYYWNEATNPLGPNRCNPAGRGCECDGLRTCSSYGWCQGIGRPTSPPPPAACQ  592
                                                                     537 scytovirin   -KGPTYCRDBAKNPGGPNRCS---NSKQCDGARTCSSSGPCQGTAGHAAA  (SEQ ID NO: 1)  95
              | :|:|||||  ||| ||||| s|||||||||||||| |:|||||
CL-B         QKSASYYWNBAKNPLGPNHRCNPAGRGCBCDGLRTCSQYGFWCQGTAHTRRA  (SEQ ID NO: 2)  642
                                                                              593
```

FIGURE 3

SEQUENCE LISTING

<160> NUMBER OF SEQ ID NOS: 7

<210> SEQ ID NO 1
<211> LENGTH: 95
<212> TYPE: PRT
<213> ORGANISM: Scytonema varium
<220> FEATURE:
<221> NAME/KEY: MISC_FEATURE
<222> LOCATION: (7)..(55)
<223> OTHER INFORMATION: Disulfide cross-link between Cys at position 7
      and Cys at position 55
<220> FEATURE:
<221> NAME/KEY: MISC_FEATURE
<222> LOCATION: (20)..(26)

```
<223> OTHER INFORMATION: Disulfide cross-link between Cys at position 20
      and Cys at position 26
<220> FEATURE:
<221> NAME/KEY: MISC_FEATURE
<222> LOCATION: (32)..(38)
<223> OTHER INFORMATION: Disulfide cross-link between Cys at position 32
      and Cys at position 38
<220> FEATURE:
<221> NAME/KEY: MISC_FEATURE
<222> LOCATION: (68)..(74)
<223> OTHER INFORMATION: Disulfide cross-link between Cys at position 68
      and Cys at position 74
<220> FEATURE:
<221> NAME/KEY: MISC_FEATURE
<222> LOCATION: (80)..(86)
<223> OTHER INFORMATION: Disulfide cross-link between Cys at position 80
      and Cys at position 86

<400> SEQUENCE: 1

Gly Ser Gly Pro Thr Tyr Cys Trp Asn Glu Ala Asn Asn Pro Gly Gly
1               5                   10                  15

Pro Asn Arg Cys Ser Asn Asn Lys Gln Cys Asp Gly Ala Arg Thr Cys
            20                  25                  30

Ser Ser Ser Gly Phe Cys Gln Gly Thr Ser Arg Lys Pro Asp Pro Gly
        35                  40                  45

Pro Lys Gly Pro Thr Tyr Cys Trp Asp Glu Ala Lys Asn Pro Gly Gly
    50                  55                  60

Pro Asn Arg Cys Ser Asn Ser Lys Gln Cys Asp Gly Ala Arg Thr Cys
65                  70                  75                  80

Ser Ser Ser Gly Phe Cys Gln Gly Thr Ala Gly His Ala Ala Ala
            85                  90                  95

<210> SEQ ID NO 2
<211> LENGTH: 107
<212> TYPE: PRT
<213> ORGANISM: Volvox carteri

<400> SEQUENCE: 2

Gln Lys Ser Ala Ser Tyr Tyr Trp Asn Glu Ala Thr Asn Pro Leu Gly
1               5                   10                  15

Pro Asn Arg Cys Asn Pro Ala Gly Arg Gly Cys Glu Cys Asp Gly Leu
            20                  25                  30

Arg Thr Cys Ser Ser Tyr Gly Trp Cys Gln Gly Ile Ser Arg Pro Thr
        35                  40                  45

Ser Pro Pro Pro Pro Ala Ala Cys Gln Gln Lys Ser Ala Ser Tyr Tyr
    50                  55                  60

Trp Asn Glu Ala Lys Asn Pro Leu Gly Pro Asn Arg Cys Asn Pro Ala
65                  70                  75                  80

Gly Arg Gly Cys Glu Cys Asp Gly Leu Arg Thr Cys Ser Gln Tyr Gly
            85                  90                  95

Trp Cys Gln Gly Thr Ala Arg Thr Arg Arg Ala
        100                 105

<210> SEQ ID NO 3
<211> LENGTH: 42
<212> TYPE: PRT
<213> ORGANISM: Scytonema varium

<400> SEQUENCE: 3

Asn Arg Cys Ser Asn Asn Lys Gln Cys Asp Gly Ala Arg Thr Cys Ser
1               5                   10                  15
```

```
Ser Ser Gly Phe Cys Gln Gly Thr Ser Arg Lys Pro Asp Pro Gly Pro
            20                  25                  30

Lys Gly Pro Thr Tyr Cys Trp Asp Glu Ala
        35                  40

<210> SEQ ID NO 4
<211> LENGTH: 43
<212> TYPE: PRT
<213> ORGANISM: Urtica dioica

<400> SEQUENCE: 4

Gln Arg Cys Gly Ser Leu Gly Gly Gly Thr Cys Pro Gly Leu Arg
1               5                   10                  15

Cys Cys Ser Ile Trp Gly Trp Cys Gly Asp Ser Glu Pro Tyr Cys Gly
            20                  25                  30

Pro Ser Cys Glu Thr Asn Cys Trp Asp Asp Glu
        35                  40

<210> SEQ ID NO 5
<211> LENGTH: 44
<212> TYPE: PRT
<213> ORGANISM: Hevea brasiliensis

<400> SEQUENCE: 5

Glu Gln Cys Gly Arg Gln Ala Gly Gly Lys Leu Cys Pro Asn Asn Leu
1               5                   10                  15

Cys Cys Ser Gln Trp Gly Trp Cys Gly Ser Thr Asp Glu Tyr Cys Ser
            20                  25                  30

Pro Asp His Asn Cys Gln Ser Asn Cys Lys Asp Ser
        35                  40

<210> SEQ ID NO 6
<211> LENGTH: 29
<212> TYPE: PRT
<213> ORGANISM: Amaranthus caudatus

<400> SEQUENCE: 6

Gly Glu Cys Val Arg Gly Arg Cys Pro Ser Gly Met Cys Cys Ser Gln
1               5                   10                  15

Phe Gly Tyr Cys Gly Lys Gly Pro Lys Tyr Cys Gly Arg
            20                  25

<210> SEQ ID NO 7
<211> LENGTH: 44
<212> TYPE: PRT
<213> ORGANISM: Triticum aestivum

<400> SEQUENCE: 7

Ile Lys Cys Gly Ser Gln Ala Gly Gly Lys Leu Cys Pro Asn Asn Leu
1               5                   10                  15

Cys Cys Ser Gln Trp Gly Phe Cys Gly Leu Gly Ser Glu Phe Cys Gly
            20                  25                  30

Gly Gly Cys Gln Ser Gly Ala Cys Ser Thr Asp Lys
        35                  40
```

SCYTOVIRINS AND RELATED CONJUGATES, FUSION PROTEINS, NUCLEIC ACIDS, VECTORS, HOST CELLS, COMPOSITIONS, ANTIBODIES AND METHODS OF USING SCYTOVIRINS

CROSS-REFERENCE TO RELATED PATENT APPLICATIONS

This application is the U.S. national phase of International Patent Application No. PCT/US03/13991 filed on May 15, 2003, which claims to the benefit of U.S. Provisional Application No. 60/381,322 filed on May 16, 2002.

FIELD OF THE INVENTION

The present invention relates to antiviral scytovirins, fusion proteins and conjugates thereof, compositions comprising same and uses thereof to inhibit viral infections. The invention also relates to nucleic acids, vectors, host cells, compositions thereof, and methods of use thereof to inhibit viral infections. The invention further relates to antibodies.

BACKGROUND OF THE INVENTION

Viral infections remain among the most formidable causes of human and non-human animal morbidity and mortality worldwide. Effective preventions or therapies against most viral pathogens remain elusive. One of the most contemporary and catastrophic examples is the still rapidly expanding and pervasive worldwide pandemic of HIV (human immunodeficiency virus) infection and AIDS (acquired immune deficiency syndrome). Despite more than two decades of research to find effective preventative or therapeutic vaccines or drugs, surprisingly little progress has been made. The need for new effective preventative and therapeutic agents for HIV/AIDS and other potentially lethal viral diseases remains an urgent global priority.

Most efforts thus far to discover and develop new antiviral prophylactic or therapeutic drugs have focused on classical, non-peptidic "small molecules." For example, nucleoside derivatives, such as AZT, which inhibit the retroviral reverse transcriptase, were among the first clinically active agents available commercially for anti-HIV therapy. Although very useful in some patients, the utility of AZT and other available anti-HIV drugs is limited by toxicity and insufficient therapeutic indices for fully adequate therapy. Also, given the dynamics of HIV infection (Coffin, Science 267: 483-489 (1995); and Cohen, Science 267: 179 (1995)), it has become increasingly apparent that agents acting as early as possible in the viral replicative cycle are needed to inhibit infection of newly produced, uninfected immune cells generated in the body in response to the virus-induced killing of infected cells. Also, it is essential to neutralize or inhibit new infectious virus produced by infected cells. Preferably, new agents, which act directly on the virus and/or upon the early viral host-cell interactions, to prevent virus/cell attachment and/or fusion and entry of virus into the cell are needed.

Peptidic or proteinaceous agents have historically been shunned in most drug discovery and development programs, typically based upon biased considerations of physicochemical properties, in vivo absorption and disposition, immunogenicity, and the like. However, in recent years, such biases have begun to sway, due to the increasing realization that the perceived problems can be circumvented, and that peptidic molecules offer tremendous structural diversity that may be exploited for development of novel therapeutics and preventions of many different kinds of diseases. Indeed, the foundation of the biotechnology industry is built substantially upon the potential of peptide- and protein-based therapeutics.

For example, in the field of HIV therapeutics a novel "rationally" constructed peptide molecule known as T-20 (Kilby, Nat. Med. 4: 1302-1307 (1998)) has been recently shown to be a potent inhibitor of HIV/cell fusion. Early clinical trials of T-20 are revealing considerable promise for inhibiting HIV infection in vivo (Cammack, Curr. Opin. Infect. Dis. 14: 13-16 (2001)). Thus, a distinct legitimacy is emerging in the HIV field for further exploration of peptide- and protein-based prevention and therapeutics of HIV infection and disease. Further reinforcing this momentum is the increasing realization that naturally occurring, non-mammalian peptides and proteins may offer entirely unanticipated new avenues for antiviral discovery and development. An outstanding example is the remarkable HIV-inactivating protein cyanovirin-N (Boyd et al., Antimicrob. Agents Chemother. 41: 1521-1530 (1997)). This agent is currently the subject of several major antiviral development programs in the United States under federal auspices, as well as elsewhere within the commercial sector. Clearly, there is great untapped potential for discovery and development of novel, non-mammalian antiviral peptides and proteins for unprecedented uses in prevention and therapeutics of viral diseases.

Accordingly, it is an object of the present invention to provide new antiviral peptides and proteins, as well as fusion proteins and conjugates thereof, and compositions comprising same, and methods of using same to inhibit viral infections. It is also an object of the present invention to provide nucleic acids, vectors, host cells, and related compositions and methods of use thereof to inhibit viral infections. It is yet another object of the present invention to provide antibodies. These and other objects and advantages of the present invention, as well as additional inventive features, will become apparent from the description provided herein.

BRIEF SUMMARY OF THE INVENTION

The present invention provides an isolated or purified antiviral protein consisting essentially of the amino acid sequence of SEQ ID NO: 1, an amino acid sequence that is about 90% or more identical to SEQ ID NO: 1, an amino acid sequence that is about 90% or more homologous to SEQ ID NO: 1, or an antiviral fragment of any of the foregoing. Also provided is a variant of the isolated or purified antiviral protein, which comprises (i) one or more conservative or neutral amino acid substitutions and/or (ii) 1, 2 or 3 amino acid additions at the N-terminus and/or C-terminus, with the proviso that the variant has antiviral activity characteristic of the antiviral protein, which consists essentially of the amino acid sequence of SEQ ID NO: 1 and which is isolated or purified from *Scytonema varium*, to a greater or lesser extent but not negated. Similarly provided are a fusion protein of the antiviral protein or variant thereof and a conjugate of the antiviral protein or variant thereof and at least one effector component. A composition comprising (i) at least one of the foregoing and (ii) a carrier, excipient or adjuvant therefore is also provided.

The present invention further provides an isolated or purified nucleic acid consisting essentially of a nucleotide sequence encoding the amino acid sequence of SEQ ID NO: 1, an amino acid sequence that is about 90% or more identical to SEQ ID NO: 1, an amino acid sequence that is about 90% or more homologous to SEQ ID NO: 1, or an antiviral fragment of any of the foregoing, optionally in the form of a vector. Also provided is a variant of the isolated or purified nucleic acid, which comprises nucleotides encoding (i) one or more conservative or neutral amino acid substitutions and/or (ii) up to 1, 2 or 3 amino acid additions at the N-terminus and/or C-terminus, with the proviso that the encoded amino acid sequence has antiviral activity characteristic of the antiviral protein, which consists essentially of the amino acid sequence of SEQ ID NO: 1 and which is isolated or purified from Scytonema varium, to a greater or lesser extent but not negated, optionally in the form of a vector. Similarly provided is an isolated or purified nucleic acid consisting essentially of a nucleotide sequence encoding a fusion protein comprising the antiviral protein, optionally in the form of a vector.

Still further provided by the present invention is an isolated cell comprising an above-described isolated or purified nucleic acid.

A composition comprising (i) an above-described isolated or purified nucleic acid or variant thereof, optionally as part of an encoded fusion protein and/or in the form of a vector, and (ii) a carrier, excipient or adjuvant therefore is also provided.

A method of inhibiting a viral infection of a host is further provided. The method comprises administering a viral infection-inhibiting amount of at least one of the following:

(i) an isolated or purified antiviral protein consisting essentially of the amino acid sequence of SEQ ID NO: 1, an amino acid sequence that is about 90% or more identical to SEQ ID NO: 1, an amino acid sequence that is about 90% or more homologous to SEQ ID NO: 1, or an antiviral fragment of any of the foregoing, (ii) a variant of (i), which comprises (a) one or more conservative or neutral amino acid substitutions and/or (b) 1, 2 or 3 amino acid additions at the N-terminus and/or C-terminus, with the proviso that the variant has antiviral activity characteristic of the antiviral protein, which consists essentially of the amino acid sequence of SEQ ID NO: 1 and which is isolated or purified from Scytonema varium, to a greater or lesser extent but not negated, (iii) a fusion protein of (i), (iv) a fusion protein of (ii), (v) a conjugate comprising (i) and at least one effector component, (vi) a conjugate comprising (ii) and at least one effector component, (vii) a composition comprising one or more of (i)-(vi), (viii) an isolated or purified nucleic acid consisting essentially of a nucleotide sequence encoding the amino acid sequence of SEQ ID NO: 1, an amino acid sequence that is about 90% or more identical to SEQ ID NO: 1, an amino acid sequence that is about 90% or more homologous to SEQ ID NO: 1, or an antiviral fragment of any of the foregoing, optionally in the form of a vector, (ix) a variant of (viii), which comprises nucleotides encoding (a) one or more conservative or neutral amino acid substitutions and/or (b) up to 1, 2 or 3 amino acid additions at the N-terminus and/or C-terminus, with the proviso that the encoded amino acid sequence has antiviral activity characteristic of the antiviral protein, which consists essentially of the amino acid sequence of SEQ ID NO: 1 and which is isolated or purified from Scytonema varium, optionally in the form of a vector, (x) an isolated or purified nucleic acid consisting essentially of a nucleotide sequence encoding a fusion protein of (viii), optionally in the form of a vector, (xi) an isolated or purified nucleic acid consisting essentially of a nucleotide sequence encoding a fusion protein of (ix), optionally in the form of a vector, (xii) a composition comprising one or more of (viii)-(xi), and (xiii) an isolated cell comprising (viii), (ix), (x), or (xi). The method optionally further comprises the prior, simultaneous or subsequent administration, by the same route or a different route, of an antiviral agent or another agent that is efficacious in inhibiting the viral infection.

Still further provided is a method of inhibiting a virus in a biological sample or in/on an inanimate object. The method comprises contacting the biological sample or the inanimate object with a viral-inhibiting amount of at least one of the following:

(i) an isolated or purified antiviral protein consisting essentially of the amino acid sequence of SEQ ID NO: 1, an amino acid sequence that is about 90% or more identical to SEQ ID NO: 1, an amino acid sequence that is about 90% or more homologous to SEQ ID NO: 1, or an antiviral fragment of any of the foregoing, (ii) a variant of (i), which comprises (a) one or more conservative or neutral amino acid substitutions and/or (b) 1, 2 or 3 amino acid additions at the N-terminus and/or C-terminus, with the proviso that the variant has antiviral activity characteristic of the antiviral protein, which consists essentially of the amino acid sequence of SEQ ID NO: 1 and which is isolated or purified from Scytonema varium, to a greater or lesser extent but not negated, (iii) a fusion protein of (i), (iv) a fusion protein of (ii), (v) a conjugate comprising (i) and at least one effector component, (vi) a conjugate comprising (ii) and at least one effector component, and (vii) a composition comprising one or more of (i)-(vi). The method optionally further comprises the prior, simultaneous or subsequent contacting, in the same manner or in different manner, of the biological sample or inanimate object with an antiviral agent or another agent that is efficacious in inhibiting the virus.

Yet still further provided is an antibody to scytovirin, an anti-scytovirin antibody, and a composition comprising same.

A method of inhibiting infection of a mammal with a virus is even still further provided. The method comprises administering to the mammal an anti-scytovirin antibody, or a composition comprising same, in an amount sufficient to induce in the mammal an immune response to the virus. The method optionally further comprises the prior, simultaneous or subsequent administration, by the same or a different route, of an antiviral agent or another agent that is efficacious in inducing an immune response to the virus.

BRIEF DESCRIPTION OF THE FIGURES

FIG. 2 compares the amino acid sequences of domains 1-48 and 49-95 of scytovirin (SEQ ID NO: 1). Sequence identities are indicated by vertical lines, and conserved changes by colons.

FIG. 3 aligns the amino acid sequence of scytovirin (SEQ ID NO: 1) and the homologous region of a cloned polypeptide (CL-B) (SEQ ID NO: 2) from *Volvox carteri*. Numbers to the top and bottom of the sequences indicate amino acid residue numbers. Sequence identities are indicated by vertical lines, conserved changes by colons, and gaps by dashes.

DETAILED DESCRIPTION OF THE INVENTION

Figure 1:
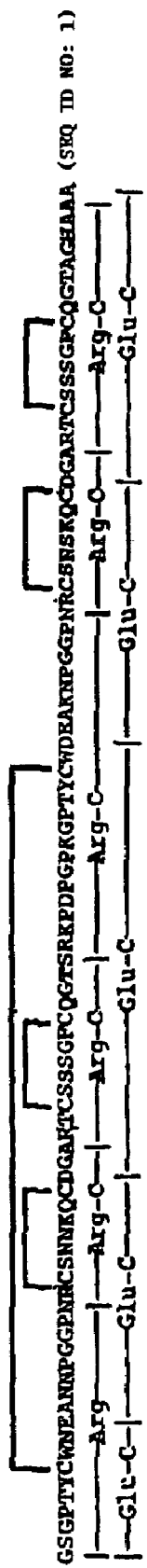
FIG. 1 shows the primary amino acid sequence (SEQ ID NO:1) of scytovirin. The protein was sequenced by a combination of N-terminal Edman degradation and ESI-MS (electrospray ionization mass spectrometry) of overlapping peptide fragments generated by endoproteinase digestions. Selected peptides isolated by $C_{18}$ HPLC (high pressure liquid chromatography) from digests with endoproteinases Arg-C and Glu-C are shown. Disulfide cross-links were determined by ESI-MS analysis of peptide fragments generated by tryptic digestion of scytovirin, and are marked (solid lines) above the sequence.

The principal overall objective of the present invention is to provide antiviral proteins and fragments thereof, as well as fusion proteins and conjugates comprising same, and broad medical uses thereof, including prophylactic and/or therapeutic applications against viruses. An initial observation, which led to the present invention, was antiviral activity in certain extracts from cultured *cyanobacteria* (blue-green algae) tested in an anti-HIV screen. The screen is one that was conceived in 1986 (by M. R. Boyd of the National Institutes of Health) and has been developed and operated at the U.S. National Cancer Institute (NCI) since 1988 (see Boyd, in AIDS, Etiology, Diagnosis, Treatment and Prevention, DeVita et al., eds., Philadelphia: Lippincott, 1988, pp. 305-317).

Cyanobacteria (blue-green algae) were specifically chosen for anti-HIV screening because they had been known to produce a wide variety of structurally unique and biologically active non-nitrogenous and amino acid-derived natural products (Faulkner, Nat. Prod. Rep. 11: 355-394 (1994); and Glombitza et al., in Algal and Cyanobacterial Biotechnology, Cresswell, R. C., et al., eds., (1989), pp. 211-218). These photosynthetic prokaryotic organisms are significant producers of cyclic and linear peptides (molecular weight generally <3 kDa), which often exhibit hepatotoxic or antimicrobial properties (Okino et al., Tetrahedron Lett. 34: 501-504 (1993); Krishnamurthy et al., PNAS USA 86: 770-774 (1989); Sivonen et al., Chem. Res. Toxicol. 5: 464-469 (1992); Carter et al., J. Org. Chem. 49: 236-241 (1984); and Frankmolle et al., J. Antibiot. 45: 1451-1457 (1992)). Sequencing studies of higher molecular weight cyanobacterial peptides and proteins have generally focused on those associated with primary metabolic processes or ones that can serve as phylogenetic markers (Suter et al., FEBS Lett. 217: 279-282 (1987); Rumbeli et al., FEBS Lett. 221: 1-2 (1987); Swanson et al., J. Biol. Chem. 267: 16146-16154 (1992); Michalowski et al., Nucleic Acids Res. 18: 2186 (1990); Sherman et al., in The Cyanobacteria, Fay et al., eds., Elsevier: New York (1987), pp. 1-33; and Rogers, in The Cyanobacteria, Fay et al., eds., Elsevier: New York (1987), pp. 35-67). The first example of a potent antiviral protein, particularly an anti-HIV protein, from a cyanobacterium was cyanovirin-N (Boyd et al., Antimicrob. Agents Chemother. 41: 1521-1530 (1997)) from *Nostoc ellipsosporum*. Otherwise, in general, proteins with antiviral properties have not been associated with cyanobacterial sources.

The cyanobacterial extract leading to the present invention was among many thousands of different extracts initially selected randomly and tested blindly in the anti-HIV screen described above. A number of these extracts had been determined preliminarily to show anti-HIV activity in the NCI screen (Patterson et al., J. Phycol. 29: 125-130 (1993)). From this group, an aqueous extract from *Scytonema varium*, which had been prepared as described (Patterson (1993), supra) and which showed an unusually high anti-HIV potency and in vitro "therapeutic index" in the NCI primary screen, was selected for detailed investigation. A specific bioassay-guided strategy was used to isolate and purify a homogenous protein highly active against HIV.

In the bioassay-guided strategy, initial selection of the extract for fractionation, as well as the decisions concerning the overall chemical isolation method to be applied, and the nature of the individual steps therein, are determined by interpretation of biological testing data. The anti-HIV screening assay (e.g., see Boyd (1988), supra; and Weislow et al., J. Natl. Cancer Inst. 81: 577-586 (1989)), which is used to guide the isolation and purification process, measures the degree of protection of human T-lymphoblastoid cells from the cytopathic effects of HIV. Fractions of the extract of interest are prepared using a variety of chemical means and are tested blindly in the primary screen. Active fractions are separated further, and the resulting subfractions are likewise tested blindly in the screen. This process is repeated as many times as necessary in order to obtain the active compound(s), i.e., antiviral fraction(s) representing pure compound(s), which then can be subjected to detailed chemical analysis and structural elucidation. Using this strategy, aqueous extracts of *Scytonema varium* were shown to contain an antiviral protein. The present invention describes more specifically a method of obtaining a wild-type scytovirin from *Scytonema varium*. Such a method comprises (a) identifying an extract of *Scytonema varium* containing antiviral activity, (b) optionally removing high molecular weight biopolymers from the extract, (c) antiviral bioassay-guided fractionating of the extract to obtain a crude extract of scytovirin, and (d) purifying the crude extract by reverse-phase HPLC to obtain a scytovirin (see, also, Example 1). More specifically, the method involves the use of an anti-HIV bioassay to guide fractionation of the extract.

A natural, wild-type scytovirin (a protein of exactly SEQ ID NO:1), which was isolated and purified as described in more detail in Example 1, was subjected to conventional procedures typically used to determine the amino acid sequence of a given pure protein. Thus, the scytovirin was initially sequenced by N-terminal Edman degradation of intact protein and numerous overlapping peptide fragments generated by endoproteinase digestion. ESI-MS of reduced, HPLC-purified, natural scytovirin showed a molecular ion consistent with the calculated value. These studies indicated that the wild-type scytovirin from *Scytonema varium* was comprised of a unique sequence of 95 amino acids having internal sequence homology, but minimal overall homology, to previously described proteins or transcription products of known nucleotide sequences (see Example 2 and FIGS. 1-5). No more than about 55% homology from wild-type scytovirin was found in any amino acid sequences or subsequences from known proteins. Given the chemically deduced amino acid sequence of wild-type scytovirin, a corresponding recombinant scytovirin can be readily created by one ordinarily skilled in the art (e.g., see below) and can be used to demonstrate further that the deduced amino acid sequence is, indeed, active against a virus, such as HIV. One skilled in the art will appreciate that functional (e.g., antiviral) scytovirin homologs can be obtained from the natural source or can be recombinantly produced.

Accordingly, the present invention provides an isolated or purified antiviral protein consisting essentially of the amino acid sequence of SEQ ID NO: 1, an amino acid sequence that is about 60%, 65%, 70%, 75%, 80%, 85% or 90% or more homologous to SEQ ID NO: 1, an amino acid sequence that is about 60%, 65%, 70%, 75%, 80%, 85% or 90% or more identical to SEQ ID NO: 1 (in which a letter indicates the standard amino acid designated by that letter; the amino acid sequence is given from left to right and top to bottom, such that the first amino acid is amino-terminal and the last amino acid is carboxyl-terminal), or an antiviral fragment of any of the foregoing. The protein preferably comprises an amino end and a carboxyl end. The protein can comprise D-amino acids, L-amino acids or a mixture of D- and L-amino acids. The D-form of the amino acids, however, is particularly preferred, since a protein comprised of D-amino acids is expected to have a greater retention of its biological activity in vivo, given that the D-amino acids are not recognized by naturally occurring proteases.

The term "isolated" as used herein means having been removed from its natural environment. The term "purified" as used herein means having been increased in purity, wherein "purity" is a relative term, and not to be construed as absolute purity. By "antiviral" is meant that the protein or fragment thereof can inhibit a virus, in particular a retrovirus, specifically a primate immunodeficiency virus, more specifically a human immunodeficiency virus (HIV), such as HIV-1, HIV-2 or SIV.

Preferably, the antiviral protein or fragment thereof is isolated or purified from *Scytonema varium*. Accordingly, the terms "scytovirin" and "scytovirins" are used herein generically to refer to an isolated or purified protein consisting essentially of SEQ ID NO: 1, as well as antiviral fragments thereof, whether isolated or purified from nature, recombinantly produced, or synthesized, and substantially identical or homologous proteins (as defined herein). An antiviral fragment can be generated, for example, by removing 1-20, preferably 1-10, more preferably 1, 2, 3, 4, or 5, and most preferably 1 or 2, amino acids from one or both ends, preferably from only one end, and most preferably from the amino-terminal end, of the wild-type scytovirin, such as wild-type scytovirin of SEQ ID NO: 1.

In view of the foregoing, the present invention provides a variant of an isolated or purified antiviral protein, wherein the variant comprises (i) one or more conservative or neutral amino acid substitutions and/or (ii) 1-20, preferably 1-10, more preferably 1, 2, 3, 4 or 5, and even more preferably, 1, 2, or 3, amino acid additions at the N-terminus and/or the C-terminus, with the proviso that the variant has antiviral activity characteristic of the antiviral protein, which consists essentially of the amino acid sequence of SEQ ID NO: 1 and which is isolated or purified from *Scytonema varium*, to a greater or lesser extent but not negated.

Alterations of the native amino acid sequence to produce variant proteins can be done by a variety of means known to those skilled in the art. For instance, amino acid substitutions can be conveniently introduced into the proteins at the time of synthesis. Alternatively, site-specific mutations can be introduced by ligating into an expression vector a synthesized oligonucleotide comprising the modified site. Alternately, oligonucleotide-directed, site-specific mutagenesis procedures can be used, such as disclosed in Walder et al., Gene 42: 133 (1986); Bauer et al., Gene 37: 73 (1985); Craik, Biotechniques, 12-19 (January 1995); and U.S. Pat. Nos. 4,518,584 and 4,737,462.

It is within the skill of the ordinary artisan to select synthetic and naturally-occurring amino acids that effect conservative or neutral substitutions for any particular naturally-occurring amino acids. The ordinarily skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids are relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the ordinarily skilled artisan can readily group synthetic amino acids with naturally-occurring amino acids.

If desired, the proteins of the invention (including antiviral fragments, variant proteins, fusion proteins, and conjugates) can be modified, for instance, by glycosylation, amidation, carboxylation, or phosphorylation, or by the creation of acid addition salts, amides, esters, in particular C-terminal esters, and N-acyl derivatives of the proteins of the invention. The proteins also can be modified to create protein derivatives by forming covalent or noncovalent complexes with other moieties in accordance with methods known in the art. Covalently-bound complexes can be prepared by linking the chemical moieties to functional groups on the side chains of amino acids comprising the proteins, or at the N- or C-terminus. Desirably, such modifications and conjugations do not adversely affect the activity of the proteins (and variants thereof). While such modifications and conjugations can have greater or lesser activity, the activity desirably is not negated and is characteristic of the unaltered protein.

The proteins (and fragments, variants and fusion proteins) can be prepared by any of a number of conventional techniques. The protein can be isolated or purified from a naturally occurring source or from a recombinant source. For instance, in the case of recombinant proteins, a DNA fragment encoding a desired protein can be subcloned into an appropriate vector using well-known molecular genetic techniques (see, e.g., Maniatis et al., *Molecular Cloning: A Laboratory Manual* 2nd ed. (Cold Spring Harbor Laboratory, 1989) and other references cited herein under "EXAMPLES"). The fragment can be transcribed and the protein subsequently translated in vitro. Commercially available kits also can be employed (e.g., such as manufactured by Clontech, Palo Alto, Calif.; Amersham Life Sciences, Inc., Arlington Heights, Ill.; InVitrogen, San Diego, Calif., and the like). The polymerase chain reaction optionally can be employed in the manipulation of nucleic acids.

Such proteins also can be synthesized using an automated peptide synthesizer in accordance with methods known in the art. Alternately, the protein (and fragments, variants, and fusion proteins) can be synthesized using standard peptide synthesizing techniques well-known to those of skill in the art (e.g., as summarized in Bodanszky, *Principles of Peptide Synthesis*, (Springer-Verlag, Heidelberg: 1984)). In particular, the protein can be synthesized using the procedure of solid-phase synthesis (see, e.g., Merrifield, J. Am. Chem. Soc., 85: 2149-54 (1963); Barany et al., Int. J. Peptide Protein Res. 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the protein from the resin can be accomplished by, for example, acid treatment at reduced temperature. The protein-containing mixture then can be extracted, for instance, with diethyl ether, to remove non-peptidic organic compounds, and the synthesized protein can be extracted from the resin powder (e.g., with about 25% w/v acetic acid). Following the synthesis of the protein, further purification (e.g., using HPLC) optionally can be done in order to eliminate any incomplete proteins, polypeptides, peptides or free amino acids. Amino acid and/or HPLC analysis can be performed on the synthesized protein to validate its identity. For other applications according to the invention, it may be preferable to produce the protein as part of a larger fusion protein, either by chemical conjugation, or through genetic means, such as are known to those skilled in the art. In this regard, the present invention also provides a fusion protein comprising the isolated or purified antiviral protein (or fragment thereof) or variant thereof and one or more other protein(s) having any desired properties or effector functions, such as cytotoxic or immunological properties, or other desired properties, such as to facilitate isolation, purification or analysis of the fusion protein. Preferably, the fusion protein comprises albumin.

A conjugate comprising (i) the isolated or purified antiviral protein (or fragment thereof) or variant thereof and (ii) at least one effector component is also provided. Preferably, the at least one effector component, which can be the same or different, is selected from the group consisting of polyethylene glycol, dextran, an immunological reagent, a toxin, an antiviral agent, and a solid support matrix.

"Immunological reagent," for example, may refer to an antibody, an immunoglobulin, or an immunological recognition element. An immunological recognition element is an element, such as a peptide, for example a FLAG octapeptide leader sequence, that can be appended to make a recombinant scytovirin-FLAG fusion protein, wherein the FLAG element facilitates, through immunological recognition, isolation and/or purification and/or analysis of the protein (or fragment thereof) or variant thereof to which it is attached.

A "toxin" can be Pseudomonas exotoxin. An "antiviral agent" can be AZT, ddI, ddC, 3TC gancyclovir, fluorinated dideoxynucleosides, nevirapine, R82913, Ro 31-8959, BI-RJ-70, acyclovir, α-interferon, recombinant sCD4, michellamines, calanolides, nonoxynol-9, gossypol and derivatives thereof, gramicidin, and cyanovirin-N or a functional homolog or derivative thereof. A "solid support matrix" can be a magnetic bead, a flow-through matrix, or a matrix comprising a contraceptive device, such as a condom, diaphragm, cervical cap, vaginal ring or sponge. In an alternative embodiment, a solid support matrix can be an implant for surgical implantation in a host and later removal.

In view of the foregoing, the present invention further provides a composition comprising (i) at least one of the isolated or purified antiviral protein (or fragment thereof), a variant thereof, a fusion protein of the antiviral protein (or fragment thereof) or variant thereof, and a conjugate of the antiviral protein (or fragment thereof) or variant thereof, and (ii) a carrier, excipient or adjuvant therefore. Preferably, component (i) of the composition is present in an antiviral effective amount and the carrier is pharmaceutically acceptable. By "antiviral effective amount" is meant an amount sufficient to inhibit the infectivity of the virus.

The carrier can be any of those conventionally used and is limited only by chemico-physical considerations, such as solubility and lack of reactivity with the active agent of the present invention, and by the route of administration. It is preferred that the pharmaceutically acceptable carrier be one which is chemically inert to the active agent and one which has no detrimental side effects or toxicity under the conditions of use. The pharmaceutically acceptable carriers described herein, for example, vehicles, adjuvants, excipients, and diluents, are well-known to those ordinarily skilled in the art and are readily available to the public. Typically, the composition, such as a pharmaceutical composition, can comprise a physiological saline solution; dextrose or other saccharide solution; or ethylene, propylene, polyethylene, or other glycol.

The present invention also provides an isolated or purified nucleic acid consisting essentially of a nucleotide sequence encoding the amino acid sequence of SEQ ID NO: 1, an amino acid sequence that is about 60%, 65%, 70%, 75%, 80%, 85% or 90% or more identical to SEQ ID NO: 1, an amino acid sequence that is about 60%, 65%, 70%, 75%, 80%, 85% or 90% or more homologous to SEQ ID NO: 1, or an antiviral fragment of any of the foregoing, optionally in the form of a vector. The terms "purified" and "isolated" have the meaning set forth above. The term "nucleic acid" as used herein means a polymer of DNA or RNA, (i.e., a polynucleotide), which can be single-stranded or double-stranded, synthesized or obtained from natural sources, and which can contain natural, non-natural or altered nucleotides.

When the above isolated or purified nucleic acid is characterized in terms of "percentage of sequence identity," a given nucleic acid molecule as described above is compared to a nucleic acid molecule encoding a corresponding gene (i.e., the reference sequence) by optimally aligning the nucleic acid sequences over a comparison window, wherein the portion of the polynucleotide sequence in the comparison window may comprise additions or deletions (i.e., gaps) as compared to the reference sequence, which does not comprise additions or deletions, for optimal alignment of the two sequences. The percentage of sequence identity is calculated by determining the number of positions at which the identical nucleic acid base occurs in both sequences, i.e., the number of matched positions, dividing the number of matched positions by the total number of positions in the window of comparison, and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information, Bethesda, Md.), or by inspection. Sequences are typically compared using BESTFIT or BlastN with default parameters.

"Substantial sequence identity" means that about 60%, preferably about 65%, more preferably about 70%, still more preferably about 75%, even more preferably about 80%, even still more preferably about 85%, and most preferably about 90% or more of the sequence of a given nucleic acid molecule is identical to a given reference sequence. Typically, two polypeptides are considered to be substantially identical if about 60%, preferably about 65%, more preferably about 70%, still more preferably about 75%, even more preferably about 80%, even still more preferably about 85%, and most preferably about 90% or more of the amino acids of which the polypeptides are comprised are identical to or represent conservative substitutions of the amino acids of a given reference sequence.

Another indication that polynucleotide sequences are substantially identical is if two molecules selectively hybridize to each other under stringent conditions. The phrase "selectively hybridizing to" refers to the selective binding of a single-stranded nucleic acid probe to a single-stranded target DNA or RNA sequence of complementary sequence when the target sequence is present in a preparation of heterogeneous DNA and/or RNA. Stringent conditions are sequence-dependent and will be different in different circumstances. Generally, stringent conditions are selected to be about 20° C. lower than the thermal melting point (Tm) for the specific sequence at a defined ionic strength and pH. The Tm is the temperature (under defined ionic strength and pH) at which 50% of the target sequence hybridizes to a perfectly matched probe.

In view of the above, "stringent conditions" preferably allow up to about 25% mismatch, more preferably up to about 15% mismatch, and most preferably up to about 10% mismatch. "At least moderately stringent conditions" preferably allow for up to about 40% mismatch, more preferably up to about 30% mismatch, and most preferably up to about 20% mismatch. "Low stringency conditions" preferably allow for up to about 60% mismatch, more preferably up to about 50% mismatch, and most preferably up to about 40% mismatch. Hybridization and wash conditions that result in such levels of stringency can be selected by the ordinarily skilled artisan using the references cited under "EXAMPLES" among others.

One of ordinary skill in the art will appreciate, however, that two polynucleotide sequences can be substantially different at the nucleic acid level, yet encode substantially similar, if not identical, amino acid sequences, due to the degeneracy of the genetic code. The present invention is intended to encompass such polynucleotide sequences.

With respect to the isolated or purified nucleic acid of the present invention, it is preferred that no insertions, deletions, inversions, and/or substitutions are present in the nucleic acid. However, it may be suitable in some instances for the isolated or purified nucleic acid to encode one or more conservative and/or neutral amino acid substitutions and/or amino acid additions at the N-terminus and/or C-terminus. In this regard, the present invention further provides a variant of the above-described isolated or purified nucleic acid, wherein the variant comprises nucleotides encoding (i) one or more conservative or neutral amino acid substitutions and/or (ii) up to 20, preferably up to 10, more preferably 1, 2, 3, 4 or 5, and even more preferably, 1, 2, or 3, amino acid additions at the N-terminus and/or the C-terminus, with the proviso that the encoded amino acid sequence has antiviral activity characteristic of the antiviral protein, which consists essentially of the amino acid sequence of SEQ ID NO: 1 and which is isolated or purified from *Scytonema varium*, to a greater or lesser extent but not negated, optionally in the form of a vector.

A variety of techniques used to synthesize the oligonucleotides of the present invention are known in the art. See, for example, Lemaitre et al., PNAS USA 84: 648-652 (1987).

Given the present disclosure, it will be apparent to one ordinarily skilled in the art that certain modified scytovirin gene sequences will code for a fully functional, i.e., antiviral, such as anti-HIV, scytovirin homolog. A minimum essential DNA coding sequence(s) for a functional scytovirin can readily be determined by one skilled in the art, for example, by synthesis and evaluation of sub-sequences comprising the wild-type scytovirin, and by site-directed mutagenesis studies of the scytovirin DNA coding sequence.

In view of the above, the present invention also provides a vector comprising an above-described isolated or purified nucleic acid molecule, optionally as part of an encoded fusion protein. The vector can be targeted to a cell-surface receptor if so desired. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987) and the references cited herein under "EXAMPLES"). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid as described above or a portion thereof ligated to a replication system functional in a prokaryotic or eukaryotic host cell. Replication systems can be derived from ColE1, 2 mµ plasmid, λ, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

One of ordinary skill in the art will appreciate that any of a number of vectors known in the art are suitable for use in the invention. Suitable vectors include those designed for propagation and expansion or for expression or both. Examples of suitable vectors include, for instance, plasmids, plasmid-liposome complexes, and viral vectors, e.g., parvoviral-based vectors (i.e., adeno-associated virus (AAV)-based vectors), retroviral vectors, herpes simplex virus (HSV)-based vectors, and adenovirus-based vectors. Any of these expression constructs can be prepared using standard recombinant DNA techniques described in, e.g., Sambrook et al., Molecular Cloning: A Laboratory Manual, $2^{nd}$ edition, Cold Spring Harbor Laboratory Press, Cold Spring Harbor, N.Y. (1989); Ausubel et al., Current Protocols in Molecular Biology, Greene Publishing Associates and John Wiley & Sons, New York, N.Y. (1994); Fischer et al., Transgenic Res. 9(4-5): 279-299 (2000); Fischer et al., J. Biol. Regul. Homeost. Agents 14: 83-92 (2000); deWilde et al., Plant Molec. Biol. 43: 347-359 (2000); Houdebine, Transgenic Research 9: 305-320 (2000); Brink et al., Theriogenology 53: 139-148 (2000); Pollock et al., J. Immunol. Methods 231: 147-157 (1999); Conrad et al., Plant Molec. Biol. 38: 101-109 (1998); Staub et al., Nature Biotech. 18: 333-338 (2000); McCormick et al., PNAS USA 96: 703-708 (1999); Zeitlin et al., Nature Biotech. 16: 1361-1364 (1998); Tacker et al., Microbes and Infection 1: 777-783 (1999); and Tacket et al., Nature Med. 4(5): 607-609 (1998). Examples of cloning vectors include the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121 and pBIN19 (Clonetech, Palo Alto, Calif.). Examples of animal expression vectors include pEUK-C1, pMAM and pMAM-neo (Clonetech).

An expression vector can comprise a native or normative promoter operably linked to an isolated or purified nucleic acid as described above. The selection of promoters, e.g., strong, weak, inducible, tissue-specific and developmental-specific, is within the skill in the art. Similarly, the combining of a nucleic acid molecule as described above with a promoter is also within the skill in the art.

Optionally, the isolated or purified nucleic acid molecule, upon linkage with another nucleic acid molecule, can encode a fusion protein, such as a fusion protein containing a functional scytovirin component plus a fusion component conferring additional desired attribute(s) to the composite protein. For example, a fusion sequence for a toxin or immunological reagent, as defined above, can be added to facilitate purification and analysis of the functional protein (e.g., such as a FLAG-scytovirin fusion protein) or for specific targeting to a virus or viral-infected cells, e.g., HIV and/or HIV-infected cells. In these instances, the scytovirin moiety serves not only as antiviral or as a neutralizing agent but also as a targeting agent to direct the effector activities of these molecules selectively against a given virus, such as HIV. Thus, for example, a therapeutic agent can be obtained by combining the HIV-targeting function of a functional scytovirin with a toxin aimed at neutralizing infectious virus and/or by destroying cells producing infectious virus, such as HIV. Similarly, a therapeutic agent can be obtained, which combines the viral-targeting function of a scytovirin with the multivalency and effector functions of various immunoglobulin subclasses. Example 4 further illustrates the viral-targeting, specifically viral envelope glycoprotein targeting, properties of a scytovirin.

The generation of fusion proteins is within the ordinary skill in the art (see, e.g., Chaudhary et al. (1988), supra, and the references cited under "EXAMPLES") and can involve the use of restriction enzyme or recombinational cloning techniques (see, e.g., Gateway™ (Invitrogen, Carlsbad, Calif.)). See, also, U.S. Pat. No. 5,314,995. In a transcriptional gene fusion, the DNA or cDNA will contain its own control sequence directing appropriate production of protein (e.g., ribosome binding site, translation initiation codon, etc.), and the transcriptional control sequences (e.g., promoter elements and/or enhancers) will be provided by the vector. In a translational gene fusion, transcriptional control sequences as well as at least some of the translational control sequences (i.e., the translational initiation codon) will be provided by the vector. In the case of a translational gene fusion, a chimeric protein will be produced.

Viral-targeted conjugates also can be prepared by chemical coupling of the targeting component with an effector component. The most feasible or appropriate technique to be used to construct a given scytovirin conjugate will be selected based upon consideration of the characteristics of the particular effector molecule selected for coupling to a scytovirin. For example, with a selected non-proteinaceous effector component, chemical coupling may be the only feasible option for creating the desired scytovirin conjugate.

Examples of effector components or other functional reagents suitable for chemical coupling to a scytovirin and thereby used as effector components in the present inventive conjugates can include, for example, polyethylene glycol, dextran, albumin, a solid support matrix, and the like, whose intended effector functions may include one or more of the following: to improve stability of the conjugate; to increase the half-life of the conjugate; to increase resistance of the conjugate to proteolysis; to decrease the immunogenicity of the conjugate; to provide a means to attach or immobilize a functional scytovirin onto a solid support matrix (e.g., see, for example, Harris, in Poly(Ethylene Glycol) Chemistry: Biotechnical and Biomedical Applications, Harris, ed., Plenum Press: New York (1992), pp. 1-14); to immobilize the scytovirin (i.e., in such instance the solid support matrix is an effector component of the scytovirin conjugate). Conjugates furthermore can comprise a functional scytovirin coupled to more than one effector component, each of which, optionally, can have different effector functions (e.g., such as a toxin molecule or an immunological reagent, and a polyethylene glycol or dextran or albumin molecule, and a solid support matrix). Diverse applications and uses of functional proteins and peptides, such as in the present instance a functional scytovirin, attached to or immobilized on a solid support matrix, are exemplified more specifically for poly(ethylene glycol) conjugated proteins or peptides in a review by Holmberg et al. (In Poly(Ethylene Glycol) Chemistry: Biotechnical and Biomedical Applications, Harris, ed., Plenum Press: New York (1992), pp. 303-324). Preferred examples of solid support matrices include magnetic beads, a flow-through matrix, and a matrix comprising a contraceptive device, such as a condom, a diaphragm, a cervical cap, a vaginal ring or a sponge.

Example 4 further reveals the specificity of effects of a scytovirin on viral molecular targets, particularly the envelope glycoproteins, especially gp120. Example 5 exemplifies the range of antiviral activity of a representative scytovirin against different $CD4^+$-tropic immunodeficiency virus strains in different target cells. Clinical isolates and laboratory strains have essentially equivalent sensitivity to the scytovirins. Cocultivation of chronically infected and uninfected CEM-SS cells with scytovirin causes a concentration-dependent inhibition of cell-to-cell fusion and virus transmission; similarly, binding and fusion inhibition assays employing HeLa-CD4-LTR-β-galactosidase cells also confirm scytovirin inhibition of virus-cell and/or cell-cell binding.

In addition to using the aforementioned assays, the antiviral, e.g., anti-HIV, activity of the scytovirins and conjugates thereof of the present invention can be further demonstrated in a series of interrelated in vitro antiviral assays (Gulakowski et al., J. Virol. Methods 33: 87-100 (1991), which accurately predict for antiviral activity in humans. These assays measure the ability of compounds to prevent the replication of HIV and/or the cytopathic effects of HIV on human target cells. These measurements directly correlate with the pathogenesis of HIV-induced disease in vivo, and, therefore, establish the utility of the present invention.

The scytovirins, and antiviral fragments, fusion proteins and conjugates thereof, of the present invention can be shown to inhibit a virus, specifically a retrovirus, more specifically an immunodeficiency virus, such as the human immunodeficiency virus, i.e., HIV-1 or HIV-2. The present inventive agents can be used to inhibit other retroviruses as well as other viruses (see, e.g., Principles of Virology: Molecular Biology, Pathogenesis, and Control, Flint et al., eds., ASM Press: Washington, D.C., 2000, particularly Chapter 19). Examples of viruses include, but are not limited to, for example, one or more of the following: Type C and Type D retroviruses, HTLV-1, HTLV-2, HIV, FIV, FLV, SIV, MLV, BLV, BIV, equine infectious virus, anemia virus, avian sarcoma viruses, such as Rous sarcoma virus (RSV), hepatitis type A, B, non-A and non-B viruses, arboviruses, varicella viruses, human herpes virus (e.g., HHV-6), measles, mumps and rubella viruses, pox viruses, influenza viruses A and B, Ebola and other hemorrhagic fever viruses, and other viruses.

Thus, the present invention further provides a composition comprising (i) one or more of an above-described purified or isolated nucleic acid or variant thereof, optionally as part of an encoded fusion protein, and (ii) a carrier, excipient or adjuvant. Preferably, (i) is present in an antiviral effective amount and the composition is pharmaceutically acceptable. The composition can further comprise at least one additional active agent, such as an antiviral agent other than a scytovirin (or antiviral fragment, fusion protein or conjugate thereof), in an antiviral effective amount. Suitable antiviral agents include AZT, ddA, ddI, ddC, 3TC gancyclovir, fluorinated dideoxynucleosides, acyclovir, α-interferon, nonnucleoside analog compounds, such as nevirapine (Shih et al., PNAS 88: 9878-9882, (1991)), TIBO derivatives, such as R82913 (White et al., Antiviral Res. 16: 257-266 (1991)), Ro31-8959, BI-RJ-70 (Merigan, Am. J. Med. 90 (Suppl.4A): 8S-17S (1991)), michellamines (Boyd et al., J. Med. Chem. 37: 1740-1745 (1994)) and calanolides (Kashman et al., J. Med. Chem. 35: 2735-2743 (1992)), nonoxynol-9, gossypol and derivatives, gramicidin, cyanovirin-N and functional homologs thereof (Boyd et al. (1997), supra). Other exemplary antiviral compounds include protease inhibitors (see R. C. Ogden and C. W. Flexner, eds., Protease Inhibitors in AIDS Therapy, Marcel Dekker, NY, 2001), such as saquinavir (see I. B. Duncan and S. Redshaw, in R. C. Ogden and C. W. Flexner, supra, pp. 27-48), ritonavir (see D. J. Kempf, in R. C. Ogden and C. W. Flexner, supra, pp. 49-64), indinavir (see B. D. Dorsey and J. P. Vacca, in R. C. Ogden and C. W. Flexner, supra, pp. 65-84), nelfinavir (see S. H. Reich, in R. C. Ogden and C. W. Flexner, supra, pp. 85-100), amprenavir (see R. D. Tung, in R. C. Ogden and C. W. Flexner, supra, pp. 101-118), and anti-TAT agents. If the composition is to be used to induce an immune response, it comprises an immune response-inducing amount of the present inventive agent and can further comprise an immunoadjuvant, such as polyphosphazene polyelectrolyte.

The pharmaceutical composition can contain other pharmaceuticals, such as virucides, immunomodulators, immunostimulants, antibiotics and absorption enhancers. Exemplary immunomodulators and immunostimulants include various interleukins, sCD4, cytokines, antibody preparations, blood transfusions, and cell transfusions. Exemplary antibiotics include antifungal agents, antibacterial agents, and anti-*Pneumocystitis carnii* agents. Exemplary absorption enhancers include bile salts and other surfactants, saponins, cyclodextrins, and phospholipids (Davis (1992), supra).

An isolated cell comprising an above-described purified or isolated nucleic acid or variant thereof, optionally in the form of a vector, which is optionally targeted to a cell-surface receptor, is also provided. Examples of host cells include, but are not limited to, a human cell, a human cell line, *E. coli, B. subtilis, P. aerugenosa, S. cerevisiae,* and *N. crassa. E. coli,* in particular *E. coli* TB-1, TG-2, DH5α, XL-Blue MRF' (Stratagene), SA2821 and Y1090. Preferably, the cell is a bacterium or yeast. A preferred bacterium is lactobacillus. The above-described nucleic acid or variant thereof, optionally in the form of a vector, can be introduced into a host cell using such techniques as transfection, electroporation, transduction, micro-injection, transformation, and the like.

Thus, using an appropriate DNA coding sequence, a recombinant scytovirin can be made by genetic engineering techniques (for general background see, e.g., Nicholl, in An Introduction to Genetic Engineering, Cambridge University Press: Cambridge (1994), pp. 1-5 & 127-130; Steinberg et al., in Recombinant DNA Technology Concepts and Biomedical Applications, Prentice Hall: Englewood Cliffs, N.J. (1993), pp. 81-124 & 150-162; Sofer, in Introduction to Genetic Engineering, Butterworth-Heinemann, Stoneham, Mass. (1991), pp. 1-21 & 103-126; Old et al., in Principles of Gene Manipulation, Blackwell Scientific Publishers: London (1992), pp. 1-13 & 108-221; and Emtage, in Delivery Systems for Peptide Drugs, Davis et al., eds., Plenum Press: New York (1986), pp. 23-33). Subsequently, the recombinantly produced protein can be isolated and purified using standard techniques known in the art (e.g., chromatography, centrifugation, differential solubility, electrophoretic techniques, etc.), and assayed for antiviral activity.

Alternatively, a wild-type scytovirin can be obtained from *Scytonema varium* by non-recombinant methods (e.g., see Example 1 and above), and sequenced by conventional techniques. The sequence can then be used to design and synthesize the corresponding DNA, which can be subcloned into an appropriate expression vector and delivered into a protein-producing cell for en mass recombinant production of the desired protein.

In view of the above, the present invention provides a method of inhibiting a viral infection of a host. The method comprises administering a viral infection-inhibiting amount of at least one of the following:

(i) an isolated or purified antiviral protein consisting essentially of the amino acid sequence of SEQ ID NO: 1, an amino acid sequence that is about 90% or more identical to SEQ ID NO: 1, an amino acid sequence that is about 90% or more homologous to SEQ ID NO: 1, or an antiviral fragment of any of the foregoing, (ii) a variant of (i), which comprises (a) one or more conservative or neutral amino acid substitutions and/or (b) 1, 2 or 3 amino acid additions at the N-terminus and/or C-terminus, with the proviso that the variant has antiviral activity characteristic of the antiviral protein consisting essentially of the amino acid sequence of SEQ ID NO: 1 and isolated or purified from *Scytonema varium* to a greater or lesser extent but not negated, (iii) a fusion protein of (i), (iv) a fusion protein of (ii), (v) a conjugate comprising (i) and at least one effector component, (vi) a conjugate comprising (ii) and at least one effector component, (vii) a composition comprising one or more of (i)-(vi), (viii) an isolated or purified nucleic acid consisting essentially of a nucleotide sequence encoding the amino acid sequence of SEQ ID NO: 1, an amino acid sequence that is about 90% or more identical to SEQ ID NO: 1, an amino acid sequence that is about 90% or more homologous to SEQ ID NO: 1, or an antiviral fragment of any of the foregoing, optionally in the form of a vector, (ix) a variant of (viii), which comprises nucleotides encoding (a) one or more conservative or neutral amino acid substitutions and/or (b) up to 1, 2 or 3 amino acid additions at the N-terminus and/or C-terminus, with the proviso that the encoded amino acid sequence has antiviral activity characteristic of the antiviral protein, which consists essentially of the amino acid sequence of SEQ ID NO: 1 and which is isolated or purified from *Scytonema varium*, optionally in the form of a vector, (x) an isolated or purified nucleic acid consisting essentially of a nucleotide sequence encoding a fusion protein of (viii), optionally in the form of a vector, (xi) an isolated or purified nucleic acid consisting essentially of a nucleotide sequence encoding a fusion protein of (ix), optionally in the form of a vector, (xii) a composition comprising one or more of (viii)-(xi), and (xiii) an isolated cell comprising (viii), (ix), (x), or (xi). By "viral infection-inhibiting amount" is meant an amount of the active agent sufficient to inhibit viral infection. The dose administered to a host, such as an animal, in particular a human, in the context of the present invention should be sufficient to effect a prophylactic or therapeutic response in the individual over a reasonable time frame. The dose used to achieve a desired antiviral concentration in vivo (e.g., 0.1-1,000 nM) will be determined by the potency of the particular active agent employed, the severity of the disease state of the infected individual, as well as, in the case of systemic administration, the body weight and age of the infected individual. The size of the dose also will be determined by the existence of any adverse side effects that may accompany the particular active agent employed. It is always desirable, whenever possible, to keep adverse side effects to a minimum. The dosages of ddC and AZT used in AIDS or ARC patients have been published. A virustatic range of ddC is generally between 0.05 µM to 1.0 µM. A range of about 0.005-0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc. hours. Currently, 0.01 mg/kg body weight ddC given every 8 hrs is preferred. When given in combined therapy, the other antiviral agent, for example, can be given at the same time as the present inventive active agent or the dosing can be staggered as desired. The two drugs also can be combined in a composition. Doses of each can be less when used in combination than when either is used alone.

In terms of administration of the present inventive antiviral agents or conjugates thereof, the dosage can be in unit dosage form, such as a tablet or capsule. The term "unit dosage form" as used herein refers to physically discrete units suitable as unitary dosages for human and animal subjects, each unit containing a predetermined quantity of a scytovirin, or antiviral fragment, fusion protein or conjugate thereof, alone or in combination with other active agents, calculated in an amount sufficient to produce the desired effect in association with a pharmaceutically acceptable diluent, carrier, or vehicle.

The specifications for the unit dosage forms of the present invention depend on the particular scytovirin, or antiviral fragment, fusion protein or conjugate thereof, employed and the effect to be achieved, as well as the associated pharmacodynamics in the host. The dose administered should be an "antiviral effective amount" or an amount necessary to achieve an "effective level" in the individual patient.

Since the "effective level" is used as the preferred endpoint for dosing, the actual dose and schedule can vary, depending upon interindividual differences in pharmacokinetics, drug distribution, and metabolism. The "effective level" can be defined, for example, as the blood or tissue level (e.g., 0.1-1, 000 nM) desired in the patient that corresponds to a concentration of one or more active agents, which inhibits a virus, such as HIV, in an assay known to predict for clinical antiviral activity of chemical compounds and biological agents. The "effective level" for agents of the present invention also can vary when the present inventive active agent is used in combination with other known active agents or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it can be desirable to utilize a "mega-dosing" regimen, wherein a large dose of the scytovirin, or antiviral fragment, fusion protein or conjugate thereof, is administered, time is allowed for the drug to act, and then a suitable reagent, device or procedure is administered to the individual to inactivate or remove the drug.

The method can be used to inhibit viral infection in a host therapeutically or prophylactically. By "therapeutically" is meant that the host already has been infected with the virus. By "prophylactically" is meant that the host has not yet been infected with the virus but is at risk of being infected with the virus. Prophylactic treatment is intended to encompass any degree of inhibition of viral infection, including, but not limited to, complete inhibition, as one of ordinary skill in the art will readily appreciate that any degree in inhibition of viral infection is advantageous. Preferably, the present inventive active agent is administered before viral infection or immediately upon determination of viral infection and is continuously administered until the virus is undetectable. The method optionally further comprises the prior, simultaneous or subsequent administration, by the same route or a different route, of an antiviral agent or another agent that is efficacious in inhibiting the viral infection. Preferably, the infection is caused by a virus having as a coat protein a glycoprotein comprising a high-mannose oligosaccharide, such as an immunodeficiency virus, in which case the host is preferably a human and the immunodeficiency virus is preferably human immunodeficiency virus (HIV).

In one embodiment of the method, the isolated cell is a cell from the host, which had been previously isolated and contacted with (viii), (ix), (x) or (xi). In another embodiment of the method, the isolated cell is a cell from a homologous host. In yet another embodiment of the method, the isolated cell is a nonpathogenic bacterium or a yeast. Preferably, the nonpathogenic bacterium is a lactobacillus. The insertion of a DNA sequence of a scytovirin (or antiviral fragment thereof) or fusion protein or conjugate thereof of the present invention ex vivo into cells previously removed from a given animal, such as a mammal, in particular a human, host is within the ordinary skill in the art. Such cells express the corresponding scytovirin or fusion protein or conjugate in vivo after reintroduction into the host. The feasibility of such a therapeutic strategy to deliver a therapeutic amount of an agent in close proximity to the desired target cells and pathogens, i.e., virus, more particularly retrovirus, specifically HIV and its envelope glycoprotein gp120, has been demonstrated in studies with cells engineered ex vivo to express sCD4 (Morgan et al. (1994), supra). It is also possible that, as an alternative to ex vivo insertion of the DNA sequences of the present invention, such sequences can be inserted into cells directly in vivo, such as by use of an appropriate viral vector. Such cells transfected in vivo are expected to produce antiviral amounts of a scytovirin or fusion protein or conjugate thereof directly in vivo.

Alternatively, a DNA sequence corresponding to a scytovirin or fusion protein or conjugate thereof can be inserted into suitable nonmammalian host cells, and such host cells will express therapeutic or prophylactic amounts of a scytovirin or fusion protein or conjugate thereof directly in vivo within or onto a desired body compartment of an animal, in particular a human. In a preferred embodiment of the present invention, a method of female-controllable prophylaxis against viral infection, such as HIV infection, comprises the intravaginal administration and/or establishment of, in a female human, a persistent intravaginal population of lactobacilli that have been transformed with a coding sequence of the present invention to produce, over a prolonged time, effective virucidal levels of a scytovirin or fusion protein or conjugate thereof, directly on or within or onto the vaginal and/or cervical and/or uterine mucosa. It is noteworthy that both of the World Health Organization (WHO), as well as the U.S. National Institute of Allergy and Infectious Diseases, have pointed to the need for development of female-controlled topical microbicides, suitable for blocking the transmission of HIV, as an urgent global priority (Lange et al., Lancet 341: 1356 (1993); and Fauci, NIAID News, Apr. 27, 1995).

Scytovirins and fusion proteins and conjugates thereof collectively comprise proteins and peptides, and, as such, are particularly susceptible to hydrolysis of amide bonds (e.g., catalyzed by peptidases) and disruption of essential disulfide bonds or formation of inactivating or unwanted disulfide linkages (Carone et al., J. Lab. Clin. Med. 100: 1-14 (1982)). There are various ways to alter molecular structure, if necessary, to provide enhanced stability to the scytovirin or conjugate thereof (Wunsch, Biopolymers 22: 493-505 (1983); and Samanen, in Polymeric Materials in Medication, Gebelein et al., eds., Plenum Press: New York (1985), pp. 227-242), which may be essential for preparation and use of pharmaceutical compositions containing scytovirins or conjugates thereof for therapeutic or prophylactic applications against viruses, e.g., HIV. Possible options for useful chemical modifications of a scytovirin or fusion protein or conjugate thereof include, but are not limited to, the following (adapted from Samanen (1985), supra): (a) olefin substitution, (b) carbonyl reduction, (c) D-amino acid substitution, (d) N-methyl substitution, (e) C-methyl substitution, (f) C-C'-methylene insertion, (g) dehydro amino acid insertion, (h) retro-inverso modification, (I) N-terminal to C-terminal cyclization, and (j) thiomethylene modification. Scytovirins and fusion proteins and conjugates thereof also can be modified by covalent attachment of carbohydrate and polyoxyethylene derivatives, which are expected to enhance stability and resistance to proteolysis (Abuchowski et al., in Enzymes as Drugs, Holcenberg et al., eds., John Wiley: New York (1981), pp. 367-378).

Other important general considerations for design of delivery strategy systems and compositions, and for routes of administration, for protein and peptide drugs, such as scytovirins and fusion proteins and conjugates thereof (Eppstein, CRC Crit. Rev. Therapeutic Drug Carrier Systems 5: 99-139 (1988); Siddiqui et al., CRC Crit. Rev. Therapeutic Drug Carrier Systems 3: 195-208 (1987); Banga et al., Int. J. Pharmaceutics 48: 15-50 (1988); Sanders, Eur. J. Drug Metab. Pharmacokinetics 15: 95-102 (1990); and Verhoef, Eur. J. Drug Metab. Pharmacokinetics 15: 83-93 (1990), also apply. The appropriate delivery system for a given scytovirin or fusion protein or conjugate thereof will depend upon its particular nature, the particular clinical application, and the site of drug action. As with any protein or peptide drug, oral delivery of a scytovirin or a conjugate thereof will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it may be desirable to use an absorption-enhancing agent in combination with a given scytovirin or fusion protein or conjugate thereof. A wide variety of absorption-enhancing agents have been investigated and/or applied in combination with protein and peptide drugs for oral delivery and for delivery by other routes (Verhoef, 1990, supra; van Hoogdalem, Pharmac. Ther. 44: 407-443 (1989); Davis, J. Pharm. Pharmacol. 44(Suppl. 1): 186-190 (1992)). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as tauro-di-hydro-fusidate, (d) fatty acids, such as oleic acid and capric acid, and their derivatives, such as acylcarnitines, monoglycerides and diglycerides, (e) non-surfactants, such as unsaturated cyclic ureas, (f) saponins, (g) cyclodextrins, and (h) phospholipids.

Other approaches to enhancing oral delivery of protein and peptide drugs, such as the scytovirins and fusion proteins and conjugates thereof, can include aforementioned chemical modifications to enhance stability to gastrointestinal enzymes and/or increased lipophilicity. Alternatively, or in addition, the protein or peptide drug can be administered in combination with other drugs or substances, which directly inhibit proteases and/or other potential sources of enzymatic degradation of proteins and peptides. Yet another alternative approach to prevent or delay gastrointestinal absorption of protein or peptide drugs, such as scytovirins or fusion proteins or conjugates thereof, is to incorporate them into a delivery system that is designed to protect the protein or peptide from contact with the proteolytic enzymes in the intestinal lumen and to release the intact protein or peptide only upon reaching an area favorable for its absorption. A more specific example of this strategy is the use of biodegradable microcapsules or microspheres, both to protect vulnerable drugs from degradation, as well as to effect a prolonged release of active drug (Deasy, in Microencapsulation and Related Processes, Swarbrick, ed., Marcell Dekker, Inc.: New York (1984), pp. 1-60, 88-89, 208-211). Microcapsules also can provide a useful way to effect a prolonged delivery of a protein and peptide drug, such as a scytovirin or conjugate thereof, after injection (Maulding, J. Controlled Release 6: 167-176 (1987)).

Given the aforementioned potential complexities of successful oral delivery of a protein or peptide drug, it is fortunate that there are numerous other potential routes of delivery of a protein or peptide drug, such as a scytovirin or fusion protein or conjugate thereof. These routes include intravenous, intraarterial, intrathecal, intracisternal, buccal, rectal, nasal, pulmonary, transdermal, vaginal, ocular, and the like (Eppstein (1988), supra; Siddiqui et al. (1987), supra; Banga et al. (1988), supra; Sanders (1990), supra; Verhoef (1990), supra; Barry, in Delivery Systems for Peptide Drugs, Davis et al., eds., Plenum Press: New York (1986), pp. 265-275; and Patton et al., Adv. Drug Delivery Rev. 8: 179-196 (1992)). With any of these routes, or, indeed, with any other route of administration or application, a protein or peptide drug, such as a scytovirin or fusion protein or conjugate thereof, may initiate an immunogenic reaction. In such situations it may be necessary to modify the molecule in order to mask immunogenic groups. It also can be possible to protect against undesired immune responses by judicious choice of method of formulation and/or administration. For example, site-specific delivery can be employed, as well as masking of recognition sites from the immune system by use or attachment of a so-called tolerogen, such as polyethylene glycol, dextran, albumin, and the like (Abuchowski et al. (1981), supra; Abuchowski et al., J. Biol. Chem. 252: 3578-3581 (1977); Lisi et al., J. Appl. Biochem. 4: 19-33 (1982); and Wileman et al., J.

Pharm. Pharmacol. 38: 264-271 (1986)). Such modifications also can have advantageous effects on stability and half-life both in vivo and ex vivo. Procedures for covalent attachment of molecules, such as polyethylene glycol, dextran, albumin and the like, to proteins, such as scytovirins or fusion proteins or conjugates thereof, are well-known to those skilled in the art, and are extensively documented in the literature (e.g., see Davis et al., In Peptide and Protein Drug Delivery, Lee, ed., Marcel Dekker: New York (1991), pp. 831-864).

Other strategies to avoid untoward immune reactions can also include the induction of tolerance by administration initially of only low doses. In any event, it will be apparent from the present disclosure to one skilled in the art that, for any particular desired medical application or use of a scytovirin or fusion protein or conjugate thereof, the skilled artisan can select from any of a wide variety of possible compositions, routes of administration, or sites of application, what is advantageous.

The present inventive compositions can be used in the context of the present inventive method in combination with other active agents to inhibit viral infection as a result of sexual transmission. Potential agents used or being considered for use against sexual transmission of HIV are very limited; present agents in this category include, for example, nonoxynol-9 (Bird, AIDS 5: 791-796 (1991)), gossypol and derivatives (Polsky et al., Contraception 39: 579-587 (1989); Lin, Antimicrob. Agents Chemother. 33: 2149-2151 (1989); and Royer, Pharmacol. Res. 24: 407-412 (1991)), and gramicidin (Bourinbair, Life Sci./Pharmacol. Lett. 54: PL5-9 (1994); and Bourinbair et al., Contraception 49: 131-137 (1994)). The method of prevention of sexual transmission of viral infection, e.g., HIV infection, in accordance with the present invention comprises vaginal, rectal, oral, penile or other topical treatment with a viral-infection inhibiting amount of a scytovirin and/or scytovirin fusion protein and/or scytovirin conjugate, alone or in combination with another antiviral agent as described above.

Nonpathogenic commensal bacteria and yeasts also offer an attractive means of in situ delivery of scytovirins or antiviral derivatives thereof to prevent sexual transmission of viral infections. For example, lactobacilli readily populate the vagina, and indeed are a predominant bacterial population in most healthy women (Redondo-Lopez et al., Rev. Infect. Dis. 12: 856-872 (1990); Reid et al., Clin. Microbiol. Rev. 3: 335-344 (1990); Bruce and Reid, Can. J. Microbiol. 34: 339-343 (1988); Reu et al., J. Infect. Dis. 171: 1237-1243 (1995); Hilier et al., Clin. Infect. Dis. 16(Suppl 4): S273-S281; and Agnew et al., Sex. Transm. Dis. 22: 269-273 (1995)). Lactobacilli are also prominent, nonpathogenic inhabitants of other body cavities, such as the mouth, nasopharynx, upper and lower gastrointestinal tracts, and rectum.

It is well-established that lactobacilli can be readily transformed using available genetic engineering techniques to incorporate a desired foreign DNA sequence, and that such lactobacilli can be made to express a corresponding desired foreign protein (see, e.g., Hols et al., Appl. and Environ. Microbiol. 60: 1401-1413 (1994)). Therefore, within the context of the present disclosure, it will be appreciated by one skilled in the art that viable host cells containing a DNA sequence or vector of the present invention, and expressing a protein or peptide of the present invention, can be used directly as the delivery vehicle for a scytovirin or fusion protein or conjugate thereof to the desired site(s) in vivo. Preferred host cells for such delivery of scytovirins or conjugates thereof directly to desired site(s), such as, for example, to a selected body cavity, can comprise bacteria. More specifically, such host cells can comprise suitably engineered strain(s) of lactobacilli, *enterococci*, or other common bacteria, such as *E. coli*, normal strains of which are known to commonly populate body cavities. More specifically yet, such host cells can comprise one or more selected nonpathogenic strains of lactobacilli, such as those described by Andreu et al. (1995, supra), especially those having high adherence properties to epithelial cells, such as, for example, adherence to vaginal epithelial cells, and suitably transformed using the DNA sequences of the present invention.

As reviewed by McGroarty (FEMS Immunol. Med. Microbiol. 6: 251-264 (1993)) the "probiotic" or direct therapeutic application of live bacteria, particularly bacteria that occur normally in nature, more particularly lactobacilli, for treatment or prophylaxis against pathogenic bacterial or yeast infections of the urogenital tract, in particular the female urogenital tract, is a well-established concept. However, present inventive use of non-mammalian cells, particularly bacteria, more particularly lactobacilli, specifically engineered with a scytovirin gene, to express a scytovirin, is heretofore unprecedented as a method of treatment of an animal, specifically a human, to prevent infection by a virus, specifically a retrovirus, more specifically HIV-1 or HIV-2.

Elmer et al. (JAMA 275: 870-876 (1996)) have recently speculated that "genetic engineering offers the possibility of using microbes to deliver specific actions or products to the colon or other mucosal surfaces . . . other fertile areas for future study include defining the mechanisms of action of various biotherapeutic agents with the possibility of applying genetic engineering to enhance activities." Elmer et al. (1996, supra) further point out that the terms "probiotic" and "biotherapeutic agent" have been used in the literature to describe microorganisms that have antagonistic activity toward pathogens in vivo; those authors more specifically prefer the term "biotherapeutic agent" to denote "microorganisms having specific therapeutic properties."

In view of the present disclosure, one skilled in the art will appreciate that the present invention teaches an entirely novel type of "probiotic" or "biotherapeutic" treatment using specifically engineered strains of microorganisms provided herein which do not occur in nature. Nonetheless, available teachings concerning selection of optimal microbial strains, in particular bacterial strains, for conventional probiotic or biotherapeutic applications can be employed in the context of the present invention. For example, selection of optimal *lactobacillus* strains for genetic engineering, transformation, direct expression of scytovirins or fusion proteins or conjugates thereof, and direct probiotic or biotherapeutic applications, to treat or prevent viral, e.g., HIV, infection, can be based upon the same or similar criteria, such as those described by Elmer et al. (1996), supra, typically used to select normal, endogenous or "nonengineered" bacterial strains for conventional probiotic or biotherapeutic therapy. Furthermore, the recommendations and characteristics taught by McGroarty, particularly for selection of optimal *lactobacillus* strains for conventional probiotic use against female urogenital infections, are pertinent to the present invention: " . . . lactobacilli chosen for incorporation into probiotic preparations should be easy and, if possible, inexpensive to cultivate . . . strains should be stable, retain viability following freeze-drying and, of course, be non-pathogenic to the host . . . it is essential that lactobacilli chosen for use in probiotic preparations should adhere well to the vaginal epithelium . . . ideally, artificially implanted lactobacilli should adhere to the vaginal epithelium, integrate with the indigenous microorganisms present, and proliferate" (MceGroarty (1993), supra). While McGroarty's teachings specifically address selections of "normal" *lactobacillus* strains for probiotic uses against pathogenic bacterial or yeast infections of the female urogenital tract, similar considerations will apply to the selection of optimal bacterial strains for genetic engineering and "probiotic" or "biotherapeutic" application against viral infections as particularly encompassed by the present invention.

Accordingly, the method of the present invention for the prevention of sexual transmission of viral infection, e.g., HIV infection, comprises vaginal, rectal, oral, penile, or other topical, insertional, or instillational treatment with a viral infection-inhibiting amount of a scytovirin or fusion protein or conjugate thereof, and/or viable host cells transformed to express a scytovirin or conjugate thereof, alone or in combination with one or more other antiviral agents (e.g., as described above).

One skilled in the art will appreciate that various routes of administering a drug are available, and, although more than one route can be used to administer a particular drug, a particular route can provide a more immediate and more effective reaction than another route. Furthermore, one skilled in the art will appreciate that the particular pharmaceutical carrier employed will depend, in part, upon the particular scytovirin or fusion protein or conjugate thereof employed, and the chosen route of administration. Accordingly, there is a wide variety of suitable formulations of the composition of the present invention.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; oil-in-water emulsions or water-in-oil emulsions; lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels and the like containing, in addition to the active ingredient, such as, for example, freeze-dried lactobacilli or live *lactobacillus* cultures genetically engineered to directly produce a scytovirin or fusion protein or conjugate thereof of the present invention, such carriers as are known in the art. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al., Science 260: 912-915 (1993)).

The scytovirins or fusion proteins or conjugates thereof, alone or in combination with other antiviral agents, can be made into aerosol formulations or microparticulate powder formulations to be administered via inhalation. These aerosol formulations can be placed into pressurized acceptable propellants, such as dichlorodifluoromethane, propane, nitrogen and the like.

The scytovirins or fusion proteins or conjugates thereof, alone or in combinations with other antiviral agents or absorption modulators, can be made into suitable formulations for transdermal application and absorption (Wallace et al. (1993), supra). Transdermal electroporation or iontophoresis also can be used to promote and/or control the systemic delivery of the compounds and/or compositions of the present invention through the skin (e.g., see Theiss et al., Meth. Find. Exp. Clin. Pharmacol. 13: 353-359 (1991)).

Formulations for rectal administration can be presented as a suppository with a suitable base comprising, for example, cocoa butter or a salicylate. Formulations suitable for vaginal administration can be presented as pessaries, tampons, creams, gels, pastes, foams, or spray formulas containing, in addition to the active ingredient, such as, for example, freeze-dried lactobacilli or live lactobacillus cultures genetically engineered to directly produce a scytovirin or fusion protein or conjugate thereof of the present invention, such carriers as are known in the art to be appropriate. Similarly, the active ingredient can be combined with a lubricant as a coating on a condom. Indeed, preferably, the active ingredient is applied to and/or delivered by any contraceptive device, including, but not limited to, a condom, a diaphragm, a cervical cap, a vaginal ring and a sponge.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The present invention further provides a method of inhibiting a virus in a biological sample or in/on an inanimate object. The method comprises contacting the biological sample or the inanimate object with a viral-inhibiting amount of at least one of the following:

(i) an isolated or purified antiviral protein consisting essentially of the amino acid sequence of SEQ ID NO: 1, an amino acid sequence that is about 90% or more identical to SEQ ID NO: 1, an amino acid sequence that is about 90% or more homologous to SEQ ID NO: 1, or an antiviral fragment of any of the foregoing, (ii) a variant of (i), which comprises (a) one or more conservative or neutral amino acid substitutions and/or (b) 1, 2 or 3 amino acid additions at the N-terminus and/or C-terminus, with the proviso that the variant has antiviral activity characteristic of the antiviral protein, which consists essentially of the amino acid sequence of SEQ ID NO: 1 and which is isolated or purified from *Scytonema varium*, to a greater or lesser extent but not negated, (iii) a fusion protein of (i), (iv) a fusion protein of (ii), (v) a conjugate comprising (i) and at least one effector component, (vi) a conjugate comprising (ii) and at least one effector component, and (vii) a composition comprising one or more of (i)-(vi). By "viral-inhibiting" amount is meant an amount of active agent, such as in the range of 0.1-1,000 nM, sufficient to inhibit the virus so as to reduce, and desirably eliminate, its infectivity. The method optionally further comprises the prior, simultaneous or subsequent contacting, in the same manner or a different manner, of the biological sample or inanimate object with an antiviral agent or another agent that is efficacious in inhibiting the virus. The biological sample can be blood, a blood product, cells, a tissue, an organ, sperm, a vaccine formulation, a bodily fluid, and the like. When the sample is a vaccine formulation, preferably the virus that is inhibited is infectious, such as HIV, although HIV, such as infectious HIV, can be inhibited in other samples in accordance with this method. The inanimate object can be a solution, a medical supply, or a medical equipment. Fusion proteins and effector components are as described above.

Formulations comprising a scytovirin or fusion protein or conjugate thereof suitable for virucidal (e.g., HIV) sterilization of inanimate objects, such as medical supplies or equipment, laboratory equipment and supplies, instruments, devices, and the like, can, for example, be selected or adapted as appropriate, by one skilled in the art, from any of the aforementioned compositions or formulations. Preferably, the scytovirin is produced by recombinant DNA technology. The scytovirin fusion protein can be produced by recombinant DNA technology, whereas the conjugate can be produced by chemical coupling of a scytovirin with an effector component as described above. Similarly, formulations suitable for ex vivo sterilization, or inhibition of virus, such as infectious virus, in a sample, such as blood, a blood product, sperm, or other bodily products, such as a fluid, cells, a tissue or an organ, or any other solution, suspension, emulsion, vaccine formulation or other material which can be administered to a patient in a medical procedure, can be selected or adapted as appropriate by one skilled in the art, from any of the aforementioned compositions or formulations. However, suitable formulations for ex vivo sterilization or inhibition of virus from a sample or in/on an inanimate object are by no means limited to any of the aforementioned formulations or compositions. For example, such formulations or compositions can comprise a functional scytovirin, such as that which is encoded by SEQ ID NO:1, or antiviral fragment, fusion protein or conjugate thereof, attached to a solid support matrix, to facilitate contacting, or otherwise inhibiting infectious virus in a sample such as described above, e.g., a bodily product such as a fluid, cells, a tissue or an organ from an organism, in particular a mammal, such as a human, including, for example, blood, a component of blood, or sperm. Preferably, the antiviral protein consists essentially of SEQ ID NO:1. Also preferably, the protein binds gp120 of HIV, in particular infectious HIV. As a more specific example, such a formulation or composition can comprise a functional scytovirin, or fusion protein or conjugate thereof, attached to (e.g., coupled to or immobilized on) a solid support matrix comprising magnetic beads, to facilitate contacting and inhibition of infectious virus, and enabling magnet-assisted removal of the bead-bound scytovirin or conjugate thereof from a sample as described above, e.g., a bodily product such as a fluid, cells, a tissue or an organ, blood, a component of blood, or sperm. Alternatively, and also preferably, the solid support matrix comprises a contraceptive device, such as a condom, a diaphragm, a cervical cap, a vaginal ring or a sponge.

As an even more specific illustration, such a composition (e.g., for ex vivo use) can comprise a functional scytovirin, or antiviral fragment, fusion protein or conjugate thereof, attached to a solid support matrix, such as magnetic beads or a flow-through matrix, by means of an anti-scytovirin antibody or at least one effector component, which can be the same or different, such as polyethylene glycol, albumin or dextran. The conjugate can further comprise at least one effector component, which can be the same or different, selected from the group consisting of an immunological reagent, a toxin and an antiviral agent. A flow-through matrix would comprise, for instance, a configuration similar to an affinity column. The scytovirin can be covalently coupled to a solid support matrix via an anti-scytovirin antibody, described below. Methods of attaching an antibody to a solid support matrix are well-known in the art (see, for example, Harlow and Lane. Antibodies: A Laboratory Manual, Cold Springs Harbor Laboratory: Cold Spring Harbor, N.Y., 1988). Alternatively, the solid support matrix, such as magnetic beads, can be coated with streptavidin, in which case the scytovirin, or a fusion protein or a conjugate thereof, is biotinylated. Such a composition can be prepared, for example, by biotinylating the scytovirin, or antiviral fragment, fusion protein or conjugate thereof, and then contacting the biotinylated scytovirin with a (commercially available) solid support matrix, such as magnetic beads, coated with streptavidin. The use of biotinylation as a means to attach a desired biologically active protein to a streptavidin-coated support matrix, such as magnetic beads, is well-known in the art. One skilled in the art will appreciate that a suitable or appropriate formulation can be selected, adapted or developed based upon the particular application at hand.

Other types of means, as are known in the art, can be used to attach a functional scytovirin (or an antiviral fragment, fusion protein or conjugate thereof as described above) to a solid support matrix, such as a magnetic bead, in which case contact with a magnet is used to separate the sample and the composition. For instance, the skilled practitioner might select a poly(ethylene glycol) molecule for attaching a functional scytovirin to a solid support matrix, thereby to provide a matrix-anchored scytovirin, wherein the scytovirin is attached to the matrix by a longer "tether" than would be feasible or possible for other attachment methods, such as biotinylation/streptavidin coupling. A scytovirin coupled by a poly(ethylene glycol) "tether" to a solid support matrix (such as magnetic beads, porous surface or membrane, and the like) can permit optimal exposure of a binding surface, epitope, hydrophobic or hydrophilic focus, and/or the like, on a functional scytovirin in a manner that, in a given situation and/or for a particular virus, facilitates inhibition of the virus.

Similarly, other types of solid support matrices can be used, such as a matrix comprising a porous surface or membrane, over or through which a sample is flowed or percolated, thereby selectively inhibiting infectious virus in the sample. The choice of solid support matrix, means of attachment of the functional scytovirin to the solid support matrix, and means of separating the sample and the matrix-anchored scytovirin will depend, in part, on the sample (e.g., fluid vs. tissue) and the virus to be inhibited. It is expected that the use of a selected coupling molecule can confer certain desired properties to a matrix, comprising a functional scytovirin coupled therewith, that may have particularly advantageous properties in a given situation.

Such methods also have utility in real time ex vivo inhibition of virus or virus infected cells in a bodily fluid, such as blood, e.g., in the treatment of viral infection, or in the inhibition of virus in blood or a component of blood, e.g., for transfusion, in the inhibition or prevention of viral infection. Such methods also have potential utility in dialysis, such as kidney dialysis, and in inhibiting virus in sperm obtained from a donor for in vitro and in vivo fertilization. The methods also have applicability in the context of tissue and organ transplantations.

The present invention also provides antibodies directed to the proteins of the present invention. The availability of antibodies to any given protein is highly advantageous, as it provides the basis for a wide variety of qualitative and quantitative analytical methods, separation and purification methods, and other useful applications directed to the subject proteins. Accordingly, given the present disclosure and the proteins of the present invention, it will be readily apparent to one skilled in the art that antibodies, in particular antibodies specifically binding to a protein of the present invention, can be prepared using well-established methodologies (e.g., such as the methodologies described in detail by Harlow and Lane, in Antibodies. A Laboratory Manual, Cold Spring Harbor Laboratory, Cold Spring Harbor, 1988, pp. 1-725). Such antibodies can comprise both polyclonal and monoclonal antibodies. Furthermore, such antibodies can be obtained and employed either in solution-phase or coupled to a desired solid-phase matrix, such as magnetic beads or a flow through matrix. Having in hand such antibodies as provided by the present invention, one skilled in the art will further appreciate that such antibodies, in conjunction with well-established procedures (e.g., such as described by Harlow and Lane (1988, supra)) comprise useful methods for the detection, quantification, or purification of a scytovirin, or antiviral fragment, fusion protein or conjugate thereof, or host cell transformed to produce the same. Example 2 further illustrates an antibody specifically binding a scytovirin. Preferably, the antibody binds to an epitope of scytovirin consisting essentially of SEQ ID NO: 1, particularly a scytovirin, which consists essentially of SEQ ID NO: 1 and which has been purified or isolated from *Scytonema varium*. In this regard, the present invention also provides a composition comprising such an antibody.

Also provided is an anti-scytovirin antibody. Preferably, the anti-scytovirin antibody has an internal image of gp120 of an immunodeficiency virus. In this regard, the present invention further provides a composition comprising such an antibody. The composition can further comprise an immunostimulant.

Matrix-anchored anti-scytovirin antibodies can be used in a method to inhibit virus in a sample. Preferably, the antibody binds to an epitope of a scytovirin consisting essentially of SEQ ID NO: 1. The antibody can be coupled to a solid support matrix using similar methods and with similar considerations as described above for attaching a scytovirin to a solid support matrix. For example, coupling methods and molecules employed to attach an anti-scytovirin antibody to a solid support matrix, such as magnetic beads or a flow-through matrix, can employ biotin/streptavidin coupling or coupling through molecules, such as polyethylene glycol, albumin or dextran. Also analogously, it can be shown that, after such coupling, the matrix-anchored anti-scytovirin antibody retains its ability to bind to a scytovirin consisting essentially of SEQ ID NO: 1, which protein can inhibit a virus. Preferably, the matrix is a solid support matrix, such as a magnetic bead or a flow-through matrix. If the solid support matrix to which the anti-scytovirin antibody is attached comprises magnetic beads, removal of the antibody-scytovirin complex can be readily accomplished using a magnet.

The present invention also provides an anti-scytovirin antibody that is anti-idiotypic in respect to gp120, i.e., has an internal image of gp120 of a primate immunodeficiency virus. Preferably, the antibody can compete with gp120 of a primate immunodeficiency virus for binding to a scytovirin. In this regard, the primary immunodeficiency virus preferably is HIV-1 or HIV-2 and the scytovirin preferably consists essentially of SEQ ID NO:1. Anti-idiotypic antibodies can be generated in accordance with methods known in the art (see, for example, Benjamin, In Immunology: a short course, Wiley-Liss, NY, 1996, pp. 436-437; Kuby, In Immunology, 3rd ed., Freeman, NY, 1997, pp. 455-456; Greenspan, et al., FASEB J. 7: 437-443 (1993); and Poskitt, Vaccine 9: 792-796 (1991)). Such an anti-idiotypic (in respect to gp120) anti-scytovirin antibody is useful in a method of inhibiting infection of an animal with a virus as provided herein.

In view of the above, a scytovirin can be administered to an animal, the animal generates anti-scytovirin antibodies, among which are antibodies that have an internal image of gp120. In accordance with well-known methods, polyclonal or monoclonal antibodies can be obtained, isolated and selected. Selection of an anti-scytovirin antibody that has an internal image of gp120 can be based upon competition between the anti-scytovirin antibody and gp120 for binding to a scytovirin, or upon the ability of the anti-scytovirin antibody to bind to a free scytovirin as opposed to a scytovirin bound to gp120. Such an anti-scytovirin antibody can be administered to an animal to inhibit a viral infection in accordance with methods provided herein. Although nonhuman anti-idiotypic antibodies, such as an anti-scytovirin antibody that has an internal image of gp120 and, therefore, is anti-idiotypic to gp120, are proving useful as vaccine antigens in humans, their favorable properties might, in certain instances, be further enhanced and/or their adverse properties further diminished, through "humanization" strategies, such as those recently reviewed by Vaughan, (Nature Biotech. 16: 535-539 (1998)). Alternatively, a scytovirin can be directly administered to an animal to inhibit a viral infection in accordance with methods provided herein such that the treated animal, itself, generates an anti-scytovirin antibody that has an internal image of gp120. The production of anti-idiotypic antibodies, such as anti-scytovirin antibody that has an internal image of gp120 and, therefore, is anti-idiotypic to gp120, in an animal to be treated is known as "anti-idiotype induction therapy," and is described by Madiyalakan et al. (Hybridoma 14: 199-203 (1995)), for example.

In view of the above, the present invention enables another method of inhibiting infection of an animal, such as a mammal, in particular a human, with a virus. The method comprises administering to the animal an anti-scytovirin antibody, or a composition comprising same, in an amount sufficient to induce in the animal an immune response to the virus, whereupon the infection of the animal with the virus is inhibited. Preferably, the anti-scytovirin antibody has an internal image of gp120 of an immunodeficiency virus with which the animal can be infected, such as a primate immunodeficiency virus. Preferably, the antibody can compete with gp120 of a primate immunodeficiency virus for binding to a scytovirin. In this regard, the primate immunodeficiency virus preferably is HIV-1 or HIV-2 and the scytovirin preferably consists essentially of SEQ ID NO:1. The method can further comprise the administration of an immunostimulant.

Also enabled by the present invention is yet another method of inhibiting infection of an animal, such as a mammal, in particular a human, with a virus. The method comprises administering to the animal a scytovirin, which binds gp120 of an immunodeficiency virus with which the animal can be infected, in an amount sufficient to induce in the animal an anti-scytovirin antibody in an amount sufficient to induce an immune response to a virus sufficient to inhibit infection of the animal with the virus. Preferably, the anti-scytovirin antibody has an internal image of gp120 of an immunodeficiency virus with which the animal can be infected, such as a primate immunodeficiency virus. Preferably, the antibody can compete with gp120 of a primate immunodeficiency virus for binding to a scytovirin. In this regard, the primate immunodeficiency virus preferably is HIV-1 or HIV-2 and the scytovirin preferably consists essentially of SEQ ID NO:1.

With respect to the above methods, sufficient amounts can be determined in accordance with methods known in the art. Similarly, the sufficiency of an immune response in the inhibition of a viral infection in an animal also can be assessed in accordance with methods known in the art.

Either one of the above methods can further comprise concurrent, pre- or post-treatment with an adjuvant to enhance the immune response, such as the prior, simultaneous or subsequent administration, by the same or a different route, of an antiviral agent or another agent that is efficacious in inducing an immune response to the virus, such as an immunostimulant. See, for example, Harlow et al., 1988, supra.

The present inventive scytovirins are further described in the context of the following examples. These examples serve to illustrate further the present invention and are not intended to limit the scope of the invention.

EXAMPLES

The following references, to the extent that they provide exemplary procedural or other details supplementary to those set forth herein, are specifically incorporated herein by reference:

Birren et al., *Genome Analysis: A Laboratory Manual Series, Volume 1, Analyzing DNA*, Cold Spring Harbor Laboratory Press, Cold Spring Harbor, N.Y. (1997), Birren et al., *Genome Analysis: A Laboratory Manual Series, Volume 2, Detecting Genes*, Cold Spring Harbor Laboratory Press, Cold Spring Harbor, N.Y. (1998), Birren et al., *Genome Analysis: A Laboratory Manual Series, Volume 3, Cloning Systems*, Cold Spring Harbor Laboratory Press, Cold Spring Harbor, N.Y. (1999), Birren et al., *Genome Analysis: A Laboratory Manual Series, Volume 4, Mapping Genomes*, Cold Spring Harbor Laboratory Press, Cold Spring Harbor, N.Y. (1999), Harlow et al., *Antibodies: A Laboratory Manual*, Cold Spring Harbor Laboratory Press, Cold Spring Harbor, N.Y. (1988), Harlow et al., *Using Antibodies: A Laboratory Manual*, Cold Spring Harbor Laboratory Press, Cold Spring Harbor, N.Y. (1999), and Sambrook et al., *Molecular Cloning: A Laboratory Manual*, 2nd edition, Cold Spring Harbor Laboratory Press, Cold Spring Harbor, N.Y. (1989).

Example 1

This example shows details of anti-HIV bioassay-guided isolation, purification and sequence elucidation of scytovirin from aqueous extracts of the cultured cyanobacterium *Scytonema varium*.

Experimental details pertinent to Example 1 as well as the subsequent Examples are as follows. All solvents were HPLC grade purchased from EM Science (Gibbstown, N.J.). Endoproteinases Arg-C and Glu-C were obtained from Roche Molecular Biochemicals (Indianapolis, Ind.). The monomeric sugars, wheat germ agglutinin, HSA, BSA, aprotinin, bovine IgG, α-acid glycoprotein and Sephadex G-100 were purchased from Sigma Corp. (St. Louis, Mo.). Oligosaccharides were purchased from Glyko, Inc. (Novato, Calif.). The rgp120 (recombinant, glycosylated, HIV-1IIIB gp120), rgp160 (recombinant, HIV-1IIIB gp160), and rgp41 (recombinant, HIV-1HxB2 gp41, ecto domain) were obtained from Advanced Biotechnologies Incorporated (Columbia, Md.). The sCD4, glycosylated and nonglycosylated gp120 (HIV-$1_{SF2}$ gp120), HIV-1 M-tropic (Ba-L) and T-tropic (IIIB) isolates were obtained from the National Institute of Allergy and Infectious Diseases AIDS Research and Reference Program, National Institutes of Health (NIH). Origins of the CEM-SS human lymphoblastoid cells and the viral strain $HIV_{RF}$ have been previously described (Gulakowski et al., J. Virol. Methods 33: 87-100 (1991)).

All HPLC separations were obtained using a Rainin SD-1 system with a Knauer variable wavelength detector monitored at 210 nm and a Rainin Dynanax $C_{18}$ 300 Å column (1×25 cm), unless otherwise stated. Electrospray ionization mass spectra were recorded on a Hewlett-Packard HP 1100 integrated LC-MS (liquid chromatograph-mass spectrometer) system equipped with an electrospray interface. Samples were introduced into the mass spectrometer at a flow rate of 0.2 mL/min with instrumental conditions as follows: nebulizer pressure ($N_2$) 25 psig; drying gas flow ($N_2$) 10 L/min; drying gas temperature, 350° C.; capillary voltage, 4,000; fragmentor voltage, 80; mass range, 250-1,600 amu.

SDS-PAGE was performed by methods previously described (Laemmli, Nature 227: 680-685 (1970)) on a Novex apparatus using a 14% polyacrylamide resolving gel (precast, Novex). Gels were run at a constant current of 25 mA/gel for 60 min at room temperature. Amino acid sequences were determined by sequential Edman degradation using an Applied Biosystems Model 494 sequencer according to the protocols of the manufacturer. The Genbank nonredundant database, BLASTP, was used to search for N-terminal amino acid sequence similarity as described (Altschul et al., Nucleic Acid Res. 25: 3389-3402 (1997)).

The method described in Weislow et al. ((1989), supra) was used to monitor and direct the isolation and purification process. Cyanobacterial culture conditions, media and classification were as described previously (Patterson, J. Phycol. 27: 530-536 (1991). Briefly, the cellular mass from a unialgal strain of *Scylonema varium* maintained at the University of Hawaii at Manoa was harvested by filtration, freeze-dried and extracted with MeOH—$CH_2Cl_2$ (1:1) followed by $H_2O$. Bioassay data indicated that only the $H_2O$ extract contained HIV-inhibitory activity.

A portion (10 g) of the aqueous extract was subjected to vacuum liquid chromatography on Bakerbond wide-pore $C_4$ media, eluting with a stepwise gradient of 0-100% methanol. A 1.0 g portion of the water/methanol 2:1 v/v fraction (3.5 g total) was loaded on a Sephadex G-100 (5.5×19 cm) column and eluted with phosphate buffer (25 mM, pH 7.5) containing 0.4 M NaCl and 0.02% $NaN_3$. Final purification was achieved using reversed-phase HPLC and eluting with a gradient of 0-60% acetonitrile in 0.05% aqueous trifluoroacetic acid (TFA) in 40 min at a flow rate of 3 mL/min, followed by 15 min of isocratic elution with 60% acetonitrile in 0.05% aqueous TFA.

To facilitate sequence and structure determinations, disulfide bonds were reduced and alkylated by methods previously described (Bokesch et al., J. Nat. Prod. 64: 249-250 (2000)). The derivatized peptide was purified by reversed-phase HPLC, using a gradient elution of 0.05% aqueous TFA for 40 min, then increasing to 60% acetonitrile in 0.05% aqueous TFA over 45 min. The S-(β-4-pyridylethyl)cysteine (PEC) derivative (250 μg) was subjected to endoproteinase Arg-C and endoproteinase Glu-C digestion per manufacturer's instructions at an enzyme/substrate ratio of 1:20. The cleaved peptide products were purified by reversed-phase HPLC, using a gradient of 0.05% aqueous TFA for 20 min, then increasing to 60% acetonitrile in 0.05% aqueous TFA over 100 min.

For disulfide bond determination a 1.0 mg sample of native, nonreduced scytovirin, 60 μl of 100 mM ammonium bicarbonate (pH 8.0), 6 μL of acetonitrile and 6 μL of a 40 μM solution of trypsin in $H_2O$ were added. The mixture was incubated at 37° C. for 16 hr, and then separated by reversed-phase HPLC, using a $C_3$ column (Zorbax) and eluting with a linear gradient from 0-100% acetonitrile in $H_2O$ with 5% $CH_3COOH$ (v/v) in the mobile phase.

The scytovirin was isolated as described above in approximately 0.03% yield, and SDS-PAGE analysis showed only a single protein band, with a relative molecular mass of about 9 kDa. ESI-MS of the protein provided a molecular weight of 9,712.8 daltons.

Reduction and alkylation of the protein as described above with 4-vinylpyridine generated the S-(β-4-pyridylethyl)cysteine (PEC) derivative, which gave an ESI-MS molecular weight of 10,774.3 daltons. This was consistent with the presence of 10 disulfide-linked cysteines. Amino acid analyses of scytovirin indicated that it contained two glutamic acid and five arginine residues. Therefore, the alkylated derivative of scytovirin was digested separately as described above with endoproteinases Arg-C and Glu-C to yield fragments amenable to N-terminal amino acid sequencing. The resulting eleven peptide fragments were sequenced, along with the intact PEC derivative, and analyzed by ESI-MS to provide the entire sequence of scytovirin (FIG. 1).

Six fragments were obtained from the endoproteinase Arg-C digest. The fragment consisting of residues 1-19 gave a molecular ion at m/z 2,096.0 (calc. m/z 2,096.2), residues 20-30 gave m/z 1,405.3 (calc. m/z 1,405.6), residues 31-43 gave m/z 1,530.4 (calc. m/z 1,530.7), residues 44-67 gave m/z 2,686.8 (calc. m/z 2,686.9), residues 68-78 gave m/z 1,378.2 (calc. m/z 1,378.6), and residues 79-95 gave m/z 1,765.7 (calc. m/z 1,766.0). These data fully supported the deduced amino acid sequence of scytovirin.

Endoproteinase Glu-C cleaved peptide bonds C-terminally at glutamic acid and aspartic acid, producing five fragments, which also supported the deduced amino acid sequence. Fragments at m/z 1,217.8, 1,998.9, 3,591.9, 1,986.2, and 2,050.0 corresponded to residues 1-10, 11-27, 28-58, 59-75, and 76-95, respectively, and provided overlapping confirmation of the amino acid sequence (FIG. 1). Therefore, it was shown that scytovirin is a 95 amino acid protein, of molecular weight 9,713 daltons, containing five intrachain disulfide bonds.

To establish the locations of the intramolecular bonds, an aliquot of nonreduced protein was treated with trypsin as described above and the resulting peptides were analyzed by ESI-MS. Peptide recognition software (http://sx102a.niddk.nih.gov/peptide) was used to determine the theoretical disulfide bonded fragments. Two disulfide links were unambiguously defined by the presence of the m/z fragments at 1318 and 1553. The program gave the single match of Cys32-Cys38 for m/z 1318. Likewise, the m/z fragment at 1553 was in agreement with Cys80-Cys86. Two possible matches for m/z 2511 were seen, with the first involving two disulfide links between the fragments consisting of amino acids 20-30 and 31 43. The second possibility consisted of one disulfide link between amino acids 20-24 and 25 43. The first option was not viable because of the already deduced disulfide bond between Cys32-Cys38, and because it was not possible to have two bonds between these fragments. The third disulfide bond was, thus, established as Cys20-Cys26.

A fragment at m/z 2,719 again gave two possible matches, one of which was two disulfide links between amino acids 68-78 and 79-95, and the other of which was, one disulfide link between amino acids 68-72 and 73-95. As a Cys80-Cys86 bond had already been assigned, it was not possible to have two disulfide links between the fragments, so a Cys68-Cys74 bond was deduced. By process of elimination, the fifth bond was assigned to Cys7-Cys55. This deduction was supported by a fragment at m/z 3,851, which corresponded to links between amino acids 51-67 and 1-19, and an additional fragment at m/z 3,158, which linked amino acids 51-60 and 1-19. Thus, the disulfide linkage pattern was identified as Cys20-Cys26, Cys32-Cys38, Cys68-Cys74, Cys80-Cys86, and Cys7-Cys55 as shown in FIG. 1.

Scytovirin shows strong internal sequence duplication. When amino acids 1-48 and 49-95 are aligned, 36 residues (78%) share direct homology and 2 (4%) represent conservative amino acid changes (FIG. 2). The bonds formed by the C20-26 and C32-38 disulfides correspond closely to those defined by the C68-74 and C80-86 disulfide links. These homologous regions, with two disulfide bridges linking cysteines located at six residue intervals, suggest the presence of two functional domains, which are linked by the C7-55 bond.

Example 2

This example describes the production of anti-scytovirin antibodies.

A New Zealand white rabbit was immunized with 100 μg of scytovirin in Freund's complete adjuvant. Booster injections of 50 μg of scytovirin in Freund's incomplete adjuvant were administered on days 13, 29, 51, 64, 100, and 195. On days 7, 21, 42, 63, 78, and 112, 10 mL of blood were removed from the rabbit. On day 112 the rabbit was sacrificed and bled out. The IgG fraction of the immune sera of the rabbit was isolated by protein-A Sepharose affinity chromatography (Bio-Rad, Hercules, Calif.) according to the manufacturer's instructions. Reactivity of the polyclonal antibodies for scytovirin was demonstrated by ELISA studies with 1:100 to 1:1,000 of the rabbit immunoglobulin fractions.

Example 3

This example illustrates the evaluation of sequence homologies of a scytovirin with known proteins, and demonstrates that scytovirin does not have strong affinity for chitin.

Figure 4:
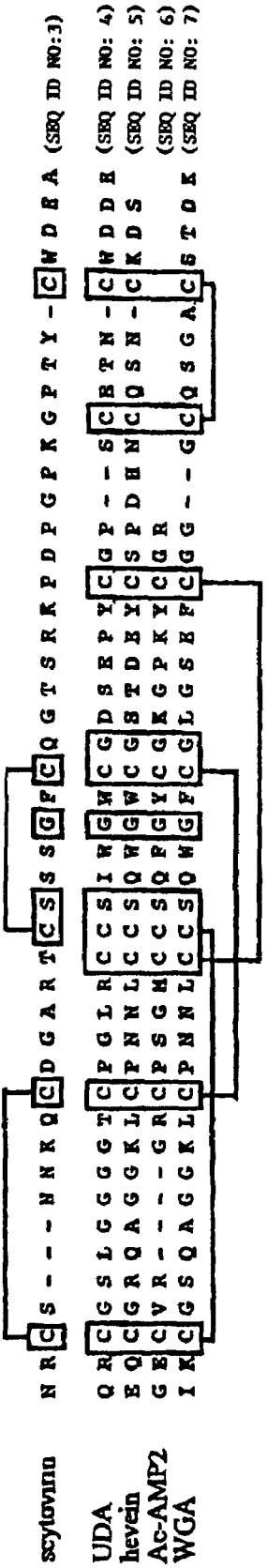
FIG. 4 aligns amino acid sequences of scytovirin (SEQ ID NO: 3) and chitin-binding domains of select lectins, namely *Urtica dioica* agglutinin (UDA; SEQ ID NO: 4), hevein from *Hevea brasiliensis* (SEQ ID NO: 5), Ac-AMP2 from *Amaranthus caudatus* (SEQ ID NO: 6), and wheat germ agglutinin (WGA) from *Triticum aestivum* (SEQ ID NO: 7). Conserved residues are in blocks. The disulfide linkage pattern is indicated below the domains for the lectins, and above for scytovirin.

A search of the BLAST database (Altschul et al., Nucleic Acid Res. 25: 3389-3402 (1997)) for identification of protein sequence homology indicated some apparent homology (55%) to a subsequence within a much larger cloned polypeptide from the multicellular green alga *Volvox carteri* (Amon et al., The Plant Cell 10: 781-789 (1998)) (FIG. 3). This polypeptide consists of three repeats of a 48-amino acid, chitin-binding domain separated by an extensin-like module from a cysteine protease domain. Of the 658 amino acids in the cloned polypeptide, scytovirin showed homology to the chitin-binding domain, which consists of a common structural motif of 30-43 amino acids with glycines and cysteines at conserved positions. Although a large number of the cysteines are conserved, scytovirin has a different disulfide bonding pattern than that of the chitin-binding domains whose disulfide bridges have been determined (FIG. 4).

Because of the homology to the inner conserved core region of chitin-binding proteins, the ability of scytovirin to bind to a chitin substrate was investigated. Scytovirin (100 μg) and wheat germ agglutinin (WGA; 100 μg) each were dissolved in 900 μL of phosphate-buffered saline (PBS) (pH 8.0) and applied to chitin microcolumns (8×10 mm). The samples were recycled three times over the columns, and eluted five times with 1 mL of PBS and once with 1.0 mL of 0.1 M acetic acid. Samples were desalted and concentrated by reversed-phase HPLC, using a gradient of 0-60% acetonitrile in 0.05% aqueous TFA over 45 min at a flow rate of 3 mL/min, before being analyzed by SDS-PAGE. Scytovirin was present in the initial fraction that was recycled through the column, while WGA was present only in the fraction eluted with low pH buffer. These results indicate that, although scytovirin contains a primary structural motif similar to the lectins and chitin-binding proteins, it does not exhibit strong binding affinity toward chitin.

Scytovirin showed a lower-scoring match (33%) to precursor proteins of Urtica dioica agglutinin (IDA; Harata et al., J. Mol. Biol. 297: 673-681 (2000)). Again, the homology was to the chitin-binding domains of UDA. Key amino acid residues involved in carbohydrate binding of UDA have been identified and include aromatic residues at positions 21, 23, and 30, and a serine at position 19 (Does et al., Plant Mol. Biol. 39: 335-347 (1999)). Scytovirin, in comparison, lacks aromatic residues at positions 21 and 30, which may interfere with carbohydrate binding activity.

A conidiospore surface protein from Trichoderma harzianum (Horwitz, direct submission to BLAST; unpublished work; GI=4585623) and cloned antifreeze proteins from Dendroides canadensis (Andorfer et al., J. Insect Phys. 46: 365-372 (2000)) and Tenebrio molitor (Liou et al., Biochemistry 38: 11415-11424 (1999)) showed lower scoring matches to scytovirin (31%, 27%, and 28%, respectively). The UDA proteins are comprised of a signal peptide with two chitin-binding domains, a hinge region and a carboxyl-terminal chitinase domain. The thermal hysteresis (antifreeze) proteins (THP), which showed homology, are a similar size (9 kDA), are Cys-, Thr-, and Ser-rich, are fully disulfide-bonded, and contain repeated sequences of 12-amino acids.

Homology to the conidiospore surface protein and the THP is due mainly to the conserved cysteines spaced at six-residue intervals. As there is no published data other than the sequence for the conidiospore protein, the function and importance of this spacing is unknown. The 12-amino acid repeat found in the THP follows this six-residue cysteine spacing and, along with other key residues, is thought to be important for the structural integrity and function of the antifreeze proteins.

Chitin-binding proteins with lectin properties are capable of cross-linking GlcNAc- or NeuNAc-containing polymers due to the presence of multiple chitin-binding domains. Since the envelope glycoprotein of HIV is heavily glycosylated, HIV infectivity and virus-cell fusion may be inhibited by lectins that are specific for the sugars present in the gp120 molecule. It has been shown that the D-mannose-specific lectin, concanavalin A (Lifson et al., J. Exp. Med. 164: 2101-2106 (1986)) does block HIV infectivity and virus-cell fusion, and the GlcNAc-specific lectins, myrianthin (Charan et al., J. Nat. Prod. 63: 1170-1174 (2000)) and UDA-1 (Balzirini et al., Antiviral Res. 18: 191-207 (1992)), are inhibitors of HIV-induced cytopathicity.

Example 4

This example illustrates viral envelope molecular target interactions of a scytovirin.

For these demonstrations, ELISA protocols were as follows. To determine the affinities of scytovirin for a series of standard proteins, 100 ng each of gp160, gp120, gp41, sCD4, bovine IgG, α-acid glycoprotein, aprotinin, HAS (human serum albumin), and BSA were subjected to an ELISA protocol as previously described (O'Keefe et al., Mol. Pharma-col. 58: 982-992 (2000)). Briefly, the proteins were bound to a 96-well plate, which was then rinsed with PBS containing 0.05% Tween 20 (TPBS) and blocked with BSA. Between each subsequent step, the plate was again rinsed with TPBS. The wells were incubated with 100 ng of scytovirin, followed by incubation with a 1:500 dilution of the anti-scytovirin rabbit polyclonal antibody preparation. The bound scytovirin was determined by adding goat-anti-rabbit antibodies conjugated to alkaline phosphatase (Roche Molecular Biochemicals, Indianapolis, Ind.). Upon addition of the alkaline phosphatase substrate buffer, absorbance was measured at 405 nm for each well. Scytovirin interacted with gp160, gp120, and to a lesser degree, gp41, but not sCD4 or other reference proteins, including bovine IgG, α-acid glycoprotein, aprotinin, HSA, and BSA.

Glycosylation-dependent binding of scytovirin to gp120 was examined using ELISA as above, with glycosylated and nonglycosylated gp120 (HIV-1$_{SF2}$ gp120) added to the 96-well plate and incubated with eight serial dilutions of scytovirin at a high concentration (100 ng/mL). Binding of scytovirin to gp120 was determined to be glycosylation-dependent.

To study the effect of monomeric and complex sugars on scytovirin and gp120 binding, ELISA plates were treated as above with the following modifications. The 96-well plates were first incubated with 100 ng of gp120 and then treated with a preincubated (1 hr) 1:1 (v/v) mixture of scytovirin/sugar to yield a final concentration of 0.005 mM scytovirin and 500 mM sugar per well. The monomeric sugars N-acetylgalactosanine, fucose, xylose, N-acetylglucosamine, mannose, glucose, and galactose were tested as well as the complex oligosaccharides mannose 7, mannose 8, mannose 9, a hybrid-type N-linked oligosaccharide, and an A3 complex-type N-linked oligosaccharide.

Scytovirin was not inhibited from binding to gp120 by N-acetylgalactosamine, fucose, xylose, N-acetylglucosamine, mannose, glucose, and galactose. Unlike the lectins, scytovirin did not show specificity for D-mannose, N-acetylglucosamine, or N-acetylgalactosamine, i.e., sugars associated with antiviral activity (Balzirini et al., Antiviral Res. 18: 191-207 (1992)). However, when tested against complex oligosaccharides, scytovirin-gp120 binding was inhibited by oligomannose 8 and oligomannose 9, but not by oligomannose 7, a hybrid-type N-linked oligosaccharide, or an A3 complex-type N-linked oligosaccharide, consistent with results recently described for cyanovirin-N (Shenoy et al., J. Pharmacol. Exp. Ther. 297: 704-710 (2001); and Bolmstedt et al., Mol. Pharmacol. 59: 949-954 (2001)), suggesting that scytovirin may interact preferentially with sites on gp120 comprising high-mannose oligosaccharides.

Although scytovirin has a lectin-like primary structure, it does not appear to belong to the chitin-binding or lectin class of proteins. It does not bind chitin, does not have the same disulfide bonding pattern as the chitin-binding domains determined thus far, and lacks some of the key aromatic amino acid residues involved in carbohydrate binding.

Example 5

This example illustrates antiviral activity, in particular anti-HIV activity, of a scytovirin.

An XTT-tetrazolium based assay was used to determine the anti-HIV activity of scytovirin on acute HIV-1 infection in CEM-SS cells as previously described (Gulakowski et al., J. Virol. Methods 33: 87-100 (1991)). The effects of scytovirin on pretreatment of CEM-SS cells and HIV-1$_{RF}$, delayed addition to HIV-1$_{RF}$ infected cells, and cell-cell fusion were studied using methods described previously (O'Keefe et al., Eur. J. Biochem. 245: 47-53 (1997)).

Antiviral assays used to study the activities of laboratory strains and primary isolates of virus have been previously published (Buckheit, Antiviral Res. 21: 247-265 (1993)). The low passage HIV-I pediatric isolate ROJO was derived as previously described (Buckheit et al., AIDS Res. Hum. Retroviruses 10: 1497-1506 (1991)). Peripheral blood mononuclear cells (PBMC) and macrophages were isolated from hepatitis and HIV sero-negative donors following Ficoll-Hypaque centrifugation as described elsewhere (Gartner, Techniques in HIV Research, Aldovini, A. and Walker, B., Eds.; Stockton Press: New York (1994), pp 59-63).

Attachment and additional fusion assays were performed as previously described with the modifications listed below. Descriptions and sources of the cell lines have been previously published (Buckheit et al., AIDS Res. Hum. Retroviruses 10: 1497-1506 (1994)). HL2/3 and HeLa CD4 LTR β-gal cell lines were maintained in Dulbecco's Minimal Essential Medium (DMEM) with 10% fetal bovine serum, penicillin (100 U/mL), streptomycin (100 µg/mL) and L-glutamine (2 mM). HeLa CD4 LTR β-gal cell lines were also supplemented with G418 (200 µg/mL) and hygromycin B (100 µg/mL). Following the interaction of HIV-1$_{IIIB}$ with HeLa CD4 LTR β-gal cells (attachment assay) or the coculture of HeLa CD4 LTR β-gal and HL2/3 cells (fusion assay), viral replication was detected by chemiluminescence using a single-step lysis and detection method (Tropix Gal-screen™, Bedford, Mass.). Viral binding to HeLa CD4 LTR β-gal cells was detected as cell-associated p24 antigen, following a 1 hr adsorption of virus and vigorous washing to remove unbound virus. Chicago Sky Blue, a polysulfonic acid dye inhibitor of HIV attachment and fusion, was used as a positive control for all assays (Clanton et al., J. Acquir. Immune Defic. Syndr. 5: 771-781 (1992)).

Scytovirin showed comparable activity against the T-tropic laboratory strain HIV-1$_{RF}$ in CEM-SS cells and primary isolate ROJO in PBMC's with EC$_{50}$ values of 0.3 nM and 7 nM. Scytovirin was also active against the M-tropic primary isolate Ba-L in macrophages, with an EC$_{50}$ value of 22 nM. Delayed addition experiments showed that scytovirin had to be present within the first 8 hr of viral infection for maximum antiviral activity, consistent with a primary effect of scytovirin on the virus/cell attachment and/or fusion process. Cell- and virus-pretreatment and delayed addition studies of scytovirin suggested that it must be continually present early in the viral life cycle to be maximally protective.

Cocultivation of uninfected and chronically infected CEM-SS cells with scytovirin caused a concentration-dependent inhibition of cell-cell fusion. Additional binding and fusion inhibition assays using β-gal indicator cells gave similar results. Scytovirin inhibited fusion of CD4+ β-gal cells with HL2/3 cells as well as the cell-free HIV-1$_{IIIB}$ fusion and infection of β-gal cells in a concentration-dependent manner.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated or purified antiviral protein comprising the amino acid sequence of SEQ ID NO: 1.

2. A fusion protein comprising the isolated or purified antiviral protein of claim 1.

3. The fusion protein of claim 2, which comprises albumin.

4. An isolated or purified nucleic acid comprising a nucleotide sequence encoding the fusion protein of claim 2, optionally in the form of a vector.

5. An isolated cell comprising the isolated or purified nucleic acid of claim 4.

6. The isolated cell of claim 5, which is a bacterium or a yeast.

7. The isolated cell of claim 6, wherein the bacterium is a lactobacillus.

8. A conjugate comprising the isolated or purified antiviral protein of claim 1 and at least one effector component.

9. The conjugate of claim 8, wherein the at least one effector component can be the same or different and is selected from the group consisting of polyethylene glycol, dextran, a toxin, an immunological reagent, an antiviral agent, and a solid support matrix.

10. A composition comprising (i) at least one isolated or purified antiviral protein of claim 1, a fusion protein thereof, and a conjugate thereof and (ii) a carrier, excipient or adjuvant therefor.

11. The composition of claim 10, wherein (i) the composition is present in an antiviral effective amount and (ii) the composition is pharmaceutically acceptable.

12. An isolated or purified nucleic acid comprising a nucleotide sequence encoding the protein of claim 1, optionally in the form of a vector.

13. An isolated cell comprising the isolated or purified nucleic acid of claim 12.

14. The isolated cell of claim 13, which is a bacterium or a yeast.

15. The isolated cell of claim 14, wherein the bacterium is lactobacillus.

16. A composition comprising (i) the isolated or purified nucleic acid of claim 12, optionally as part of an encoded fusion protein, and (ii) a carrier, excipient or adjuvant therefor.

17. The composition of claim 16, wherein (i) is present in an antiviral effective amount and the composition is pharmaceutically acceptable.

18. A method of inhibiting a viral infection of a host, which method comprises administering a viral infection-inhibiting amount of at least one of the following:
   i. an isolated or purified antiviral protein of claim 1,
   ii. a fusion protein of (i),
   iii. a conjugate comprising (i) and at least one effector component,
   iv. a composition comprising one or more of (i)-(iii),
   v. an isolated or purified nucleic acid comprising a nucleotide sequence encoding the amino acid sequence of claim 1, optionally in the form of a vector,
   vi. an isolated or purified nucleic acid comprising a nucleotide sequence encoding a fusion protein of (v), optionally in the form of a vector,
   vii. a composition comprising one or more of (v)-(vi), and an isolated cell comprising (v) or (vi),
   wherein the viral infection is caused by a virus having a glycoprotein comprising a high-mannose oligosaccharide as a coat protein,
   which method optionally further comprises the prior, simultaneous or subsequent administration, by the same route or a different route, of an antiviral agent or another agent that is efficacious in inhibiting the viral infection, whereupon the viral infection is inhibited.

19. The method of claim 18, wherein the virus is an immunodeficiency virus.

20. The method of claim 19, wherein the fusion protein comprises albumin.

21. The method of claim 19, wherein the at least one effector component can be the same or different and is selected from the group consisting of polyethylene glycol, dextran, a toxin, an immunological reagent, an antiviral agent, and a solid support matrix.

22. The method of claim 19, wherein the isolated cell is a cell from the host, which had been previously isolated and contacted with (v) or (vi).

23. The method of claim 19, wherein the isolated cell is a cell from a homologous host.

24. The method of claim 19, wherein the isolated cell is a nonpathogenic bacterium or a yeast.

25. The method of claim 18, wherein the host is a human and the immunodeficiency virus is human immunodeficiency virus (HIV).

26. The method of claim 25, wherein the fusion protein comprises albumin.

27. The method of claim 25, wherein the at least one effector component can be the same or different and is selected from the group consisting of polyethylene glycol, dextran, a toxin, an immunological reagent, an antiviral agent, and a solid support matrix.

28. The method of claim 25, wherein the isolated cell is a cell from the host, which had been previously isolated and contacted with (v) or (vi).

29. The method of claim 25, wherein the isolated cell is a cell from a homologous host.

30. The method of claim 25, wherein the isolated cell is a nonpathogenic bacterium or a yeast.

31. The method of claim 18, wherein the fusion protein comprises albumin.

32. The method of claim 18, wherein the at least one effector component can be the same or different and is selected from the group consisting of polyethylene glycol, dextran, a toxin, an immunological reagent, an antiviral agent, and a solid support matrix.

33. The method of claim 18, wherein the isolated cell is a cell from the host, which had been previously isolated and contacted with (v) or (vi).

34. The method of claim 18, wherein the isolated cell is a cell from a homologous host.

35. The method of claim 18, wherein the isolated cell is a nonpathogenic bacterium or a yeast.

36. The method of claim 35, wherein the nonpathogenic bacterium is a lactobacillus.

37. The method of claim 18, wherein the viral infection is an influenza infection.

38. The method of claim 18, wherein the viral infection is an E*bola infection*.

39. The method of claim 18, wherein the host is an avian host.

40. The method of claim 18, wherein at least one of (i)-(vii) is administered nasally, by inhalation, or by parenteral administration.

41. A method of inhibiting a virus in a biological sample or in/on an inanimate object, which method comprises contacting the biological sample or the inanimate object with a viral-inhibiting amount of at least one of the following:
   i. an isolated or purified antiviral protein of claim 1,
   ii. a fusion protein of (i),
   iii. a conjugate comprising (i) and at least one effector component,
   iv. a composition comprising one or more of (i)-(iii),
   wherein the viral infection is caused by a virus having a glycoprotein comprising a high-mannose oligosaccharide as a coat protein,
   which method optionally further comprises the prior, simultaneous or subsequent contacting, in the same manner or in a different manner, of the biological sample or inanimate object with an antiviral agent or another agent that is efficacious in inhibiting the virus, whereupon the virus is inhibited.

42. The method of claim 41, wherein the biological sample is blood, a blood product, cells, a tissue, an organ, sperm, a vaccine formulation, or a bodily fluid.

43. The method of claim 41, wherein the inanimate object is a solution, a medical supply, or a medical equipment.

44. The method of claim 41, wherein the fusion protein comprises albumin.

45. The method of claim 41, wherein the at least one effector component can be the same or different and is selected from the group consisting of polyethylene glycol, dextran, a toxin, an immunological reagent, an antiviral agent, and a solid support matrix.

46. An isolated or purified antiviral protein consisting essentially of the amino acid sequence of SEQ ID NO: 1, an amino acid sequence that is about 90% or more identical to SEQ ID NO: 1 or an amino acid sequence that is about 90% or more homologous to SEQ ID NO: 1, which has been isolated or purified from *Scytonema varium*.

* * * * *